US012674137B2

(12) United States Patent
Bacchetta et al.

(10) Patent No.: US 12,674,137 B2
(45) Date of Patent: Jul. 7, 2026

(54) FOXP3 ENGINEERED CD4+ T CELLS FOR USE IN TREG-BASED IMMUNOTHERAPY

(71) Applicants: THE BOARD OF TRUSTEES OF THE LELAND STANFORD JUNIOR UNIVERSITY, Stanford, CA (US); OSPEDALE SAN RAFFAELE S.R.L., Milan (IT); FONDAZIONE TELETHON, Rome (IT)

(72) Inventors: Rosa Bacchetta, Menlo Park, CA (US); Maria Grazia Roncarolo, Menlo Park, CA (US); Yohei Sato, Palo Alto, CA (US); Luigi Naldini, Milan (IT); Laura Passerini, Milan (IT)

(73) Assignees: THE BOARD OF TRUSTEES OF THE LELAND STANFORD RINIOR UNIVERSITY; OSPEDALE SAN RAFFAELE S.R.L, Milan (IT); FONDAZIONE TELETHON, Rome (IT)

( * ) Notice: Subject to any disclaimer, the term of this patent is extended or adjusted under 35 U.S.C. 154(b) by 1179 days.

(21) Appl. No.: 17/615,766

(22) PCT Filed: Jun. 5, 2020

(86) PCT No.: PCT/US2020/036401
§ 371 (c)(1),
(2) Date: Dec. 1, 2021

(87) PCT Pub. No.: WO2020/247805
PCT Pub. Date: Dec. 10, 2020

(65) Prior Publication Data
US 2022/0273712 A1 Sep. 1, 2022

Related U.S. Application Data

(60) Provisional application No. 62/994,454, filed on Mar. 25, 2020, provisional application No. 62/858,828, filed on Jun. 7, 2019.

(51) Int. Cl.
| | |
|---|---|
| *C12N 5/0783* | (2010.01) |
| *A61K 40/11* | (2025.01) |
| *A61K 40/22* | (2025.01) |
| *A61K 40/41* | (2025.01) |

(52) U.S. Cl.
CPC ............ *C12N 5/0637* (2013.01); *A61K 40/11* (2025.01); *A61K 40/22* (2025.01); *A61K 40/416* (2025.01); *A61K 40/418* (2025.01); *C12N 2501/2302* (2013.01); *C12N 2501/2307* (2013.01); *C12N 2501/2315* (2013.01); *C12N 2501/51* (2013.01); *C12N 2510/00* (2013.01)

(58) Field of Classification Search
CPC ...... A61K 40/11; A61K 40/30; C12N 5/0637; C12N 2501/60; C12N 2740/16043
See application file for complete search history.

(56) References Cited

U.S. PATENT DOCUMENTS 8,501,464 B2 8/2013 Naldini et al.

FOREIGN PATENT DOCUMENTS

| | | |
|---|---|---|
| WO | WO2000009693 | 2/2000 |
| WO | WO2007091066 | 8/2007 |
| WO | WO2018024894 | 2/2018 |
| WO | WO2019040655 | 2/2019 |
| WO | WO2019210042 | 10/2019 |
| WO | WO20192170078 | 10/2019 |
| WO | WO2020104467 | 5/2020 |

OTHER PUBLICATIONS

Passerini, L. and R. Bacchetta, Oct. 2017, Forkhead-Box-P3 Gene Transfer in Human CD4+ T Conventional Cells for the Generation of Stable and Efficient Regulatory T Cells, Suitable for Immune Modulatory Therapy, Front. Immunol. 8, Article 1282, pp. 1-8.*
Amendola, M., et al., Jan. 2005, Coordinate dual-gene transgenesis by lentiviral vectors carrying synthetic bidirectional promoters, Nat. Biotech. 23(1):108-116.*
Golding, M. C., and M. R. W. Mann, 2011, A bidirectional promoter architecture enhances lentiviral transgenesis in embryonic and extraembryonic stem cells, Gene Therapy 18:817-826.*
Gee, A. P., 2018, GMP CAR-T cell production, Best Practice Res. Clin. Haematol. 31:126-134.*
Poorebrahim, M., et al., 2019, Production of CAR T-cells by GMP-grade lentiviral vectors: latest advances and future prospects, Crit. Rev. Clin. Lab. Sci. 56(6):393-419.*
Bacchetta et al. (2016) "From IPEX syndrome to FOXP3 mutation: a lesson on immune dysregulation", Annals of The New York Academy of Sciences, New York Academy of Sciences, US, vol. 1417, No. 1, 25, pp. 5-22.
Goodwin et al. (2020) "CRISPR-based gene editing enables FOXP3 gene repair in IPEX patient cells", Science advances, p. 1-16, eaaz0571.
Honaker et al. (2020) "Gene editing to induce FOXP3 expression in human CD4 + T cells leads to a stable regulatory phenotype and function", Science Translational Medicine, vol. 12, No. 546, p. 1-18, eaay6422.
Lee et al (2020) "Gene editing using CRISPR enables FOXP3 gene repair in HSPCs and IPEX patient T cells", Cytotherapy, vol. 22, No. 5, p. S20, Abstract.

(Continued)

*Primary Examiner* — Jeffrey S Parkin
(74) *Attorney, Agent, or Firm* — Pamela J. Sherwood; Bozicevic, Field & Francis LLP

(57) ABSTRACT

Engineered Treg-like cells, $CD4^{LVFOXP3}$ T cells, and their use in cellular therapy to promote immune tolerance are disclosed. In particular, $CD4^{LVFOXP3}$ T cells are produced by transduction of $CD4^+$ T cells with a lentiviral vector expressing FOXP3 under the control of a constitutive promoter. Transduced cells express FOXP3 at high and persistent levels and acquire immune suppressive characteristics resembling naturally occurring Treg cells.

4 Claims, 22 Drawing Sheets

(56)           References Cited

OTHER PUBLICATIONS

Goodwin et al. (2016) "123. Gene Editing as a Therapeutic Approach to Treat IPEX Syndrome", Molecular Therapy, vol. 24, p. S51, XP093163819.

Passerini et al. (2013) "CD4+ T Cells from IPEX Patients Convert into Functional and Stable Regulatory T Cells by FOXP3 Gene Transfer", Science Translational Medicine, vol. 5, No. 215, pp. 1-10, XP093055996.

Schumann et al. (2015) "Generation of knock-in primary human T cells using Cas9 ribonucleoproteins", Proceedings of The National Academy of Sciences, vol. 112, No. 33, pp. 10437-10442.

Allan et al. (2008). "Generation of potent and stable human CD4+ T regulatory cells by activation-independent expression of FOXP3". *Molecular Therapy*, 16(1), 194-202.

Passerini et al. (2013). "CD4+ T cells from IPEX patients convert into functional and stable regulatory T cells by FOXP3 gene transfer". *Science translational medicine,*5(215), 215ra174-215ra174.

Sato et al. (2020). Human-engineered Treg-like cells suppress FOXP3-deficient T cells but preserve adaptive immune responses in vivo. *Clinical & Translational Immunology*, 9(11), e1214.

Passerini et al. (2017) "Forkhead-Box-P3 Gene Transfer in Human CD4+ T Conventional Cells for the Generation of Stable and Efficient Regulatory T Cells, Suitable for Immune Modulatory Therapy". Front Immunol., vol. 8, article 1282. pp 1-8, abstract, p. 3, col. 2, para 2-3, Table 1, Fig. 1.

Casucci et al. (2018) "Extracellular NGFR Spacers Allow Efficient Tracking and Enrichment of Fully Functional CAR-T Cells Co-Expressing a Suicide Gene". Frontiers in Immunology, vol. 9, No. 507; pp. 1-13.

Allan S.E. et al., Generation of potent and stable human CD4+ T regulatory cells by activation-independent expression of FOXP3. Molecular Therapy, vol. 16, Issue No. 1, pp. 194-202 (Jan. 1, 2008; published online Nov. 6, 2007).†

* cited by examiner
† cited by third party

FIG. 1

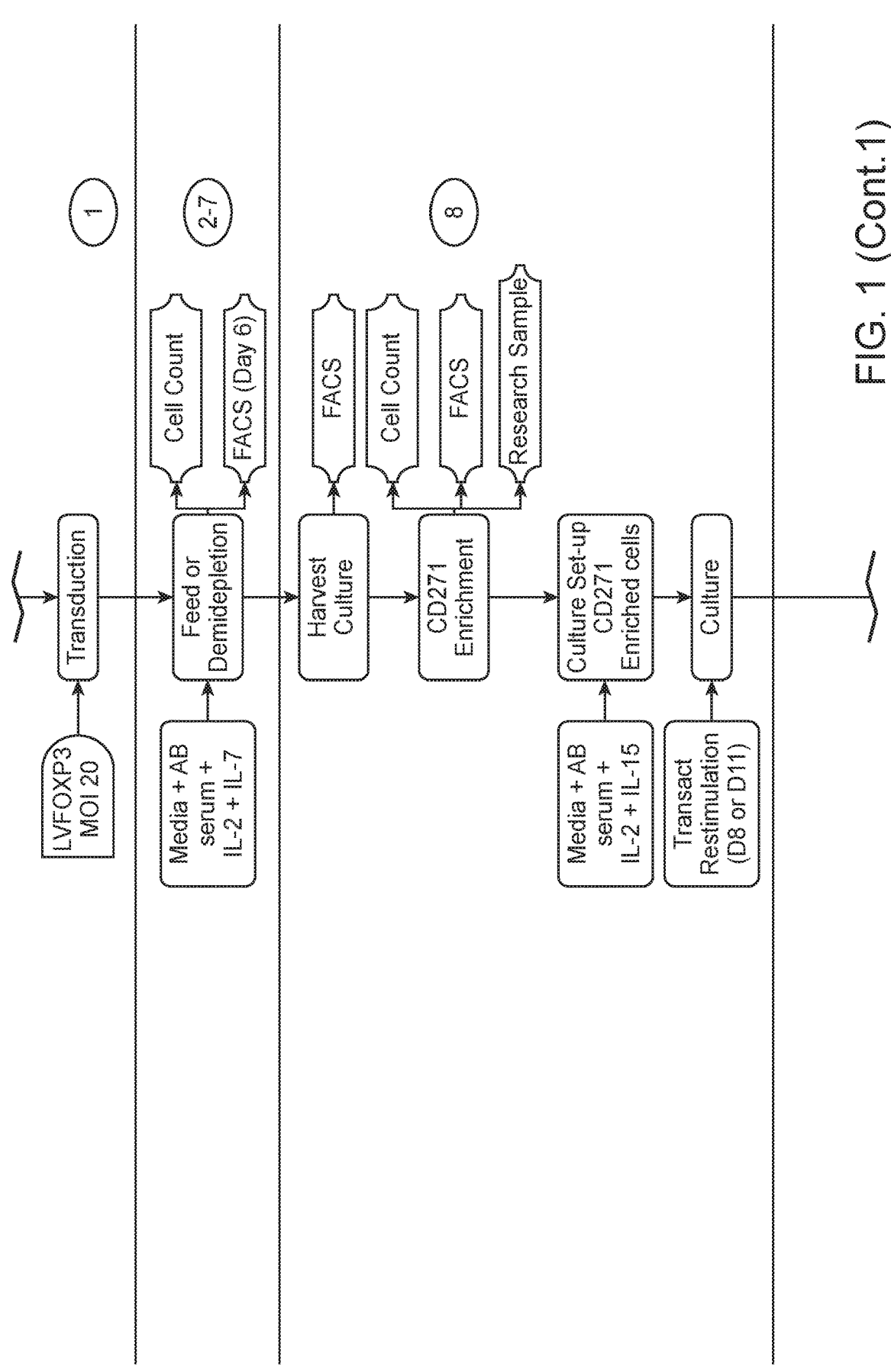
FIG. 1 (Cont.1)

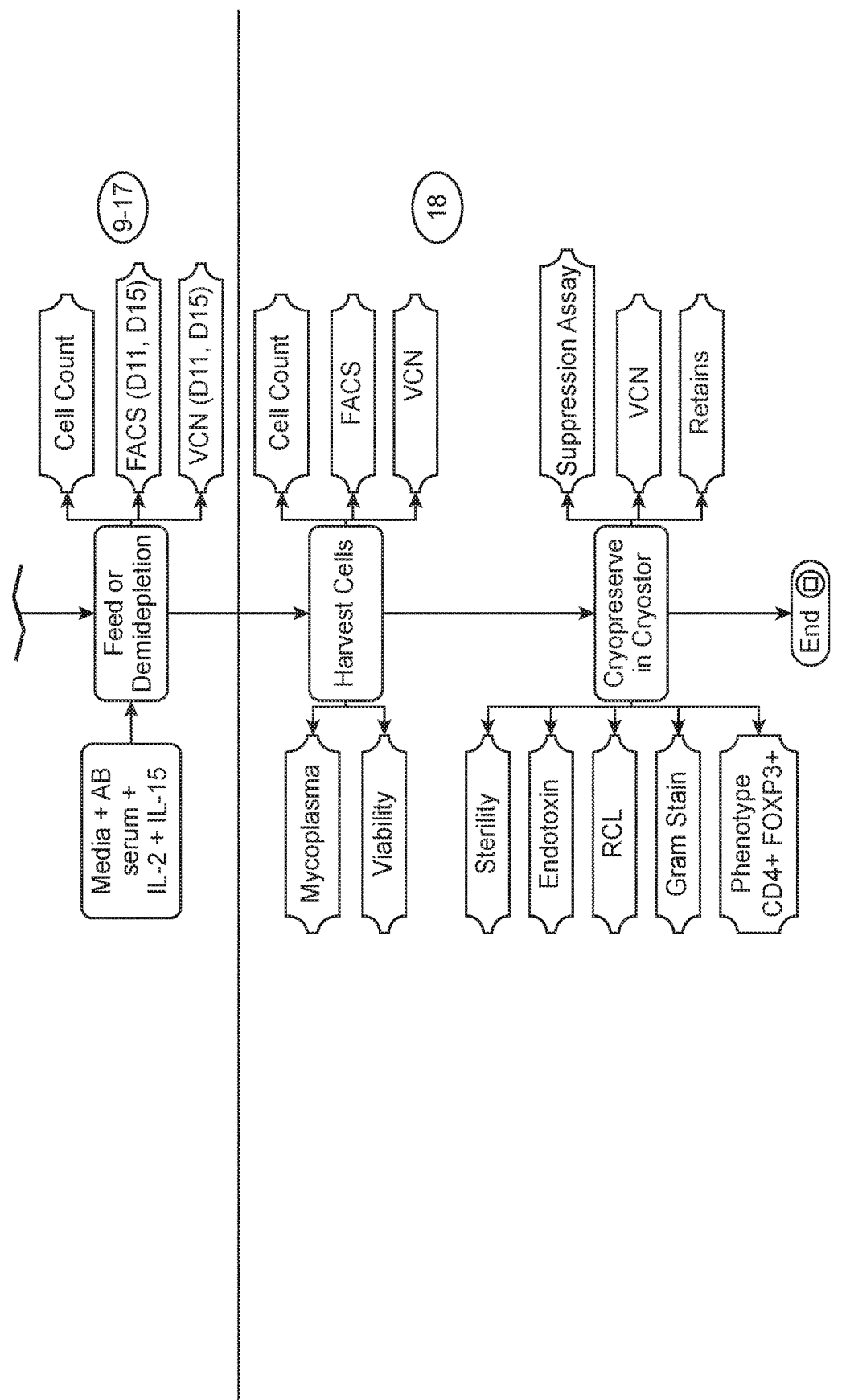
FIG. 1 (Cont.2)

| Component (position) | Description |
|---|---|
| CMV enhancer (77-456) | human cytomegalovirus (CMV) promoter enhancer |
| CMV promoter (457-649) | CMV promoter |
| 5' LTR (675-855) | 5' HIV Long Terminal Repeat |
| HIV-1 ψ (902-1027) | Required for viral gene expression, reverse transcription, and target cell genome integration |
| tGAG (983-1347) | Required for packaging of genomic transfer RNA |
| RRE (1520-1753) | HIV Rev Response Element, required for processing and transport of viral RNA |
| CPPT/CTS (2249-2366) | Central Polypurine Tract and Central Termination Sequence from HIV-1; increases transduction |
| SV40 PolyA (2503-2637) | Polyadenylation sequence from Simian Virus 40; required for transgene expression |
| NGFR (2825-3667), also referred to as deltaNGFR | Truncated nerve growth factor receptor; expressed on cell surface and required for selection of transduced cells |
| Minimal CMV promoter (3889-3927) | Human CMV immediate early promoter; internal promoter required for expression of truncated NGFR marker gene |
| EF-1a promoter (4042-5219) | Human elongation factor 1a promoter; internal promoter required for expression of therapeutic transgene FOXP3 |
| hFOXP3 cDNA (5269-6554) | Human Forkhead Box Protein 3 (FOXP3) cDNA; Therapeutic Gene of Interest |
| Mutated WPRE (6596-7184) | Woodchuck hepatitis virus posttranscriptional regulatory element; increases GOI expression efficiency by increased mRNA stability and protein synthesis. The mutated WPRE was modified to remove the WHx start codon, the modification confirmed by sequencing, and verified to not affect expression of the FOXP3 transgene following transduction in cell culture. |
| tNEF (7188-7270) | Truncated NEF sequence from HIV-1; required for high viral burden |
| 3'LTR (7271-7504) | HIV 3' Long Terminal Repeat |
| SV40 PolyA (7576-7697) | Polyadenylation sequence from SV40; required for transgene expression |
| SV40 ori (7737-7872) | SV40 origin of replication |
| KanR (8161-8976) | Kanamycin Resistance gene for plasmid growth and selection; Aminoglycocide phoshotransferase |
| Ori (9137-9725) | Bacterial high copy origin of replication for plasmid growth |

FIG. 2B

| Small Scale Runs | | CD4 | FOXP3 | NGFR | FOXP3/ NGFR |
|---|---|---|---|---|---|
| Subject ID | | (% positive) | | | |
| 2447 | fresh | 95.7 | 95.5 | 93.5 | 90.3 |
| | frozen | 94.7 | 98.8 | 89.4 | 88.7 |
| 5691 | fresh | 95.9 | 96.0 | 80.6 | 78.6 |
| | frozen | 93.8 | 93.3 | 83.9 | 79.5 |
| 5692 | fresh | 92.5 | 90.6 | 76.4 | 70.0 |
| | frozen | 88.8 | 95.2 | 76.0 | 73.4 |

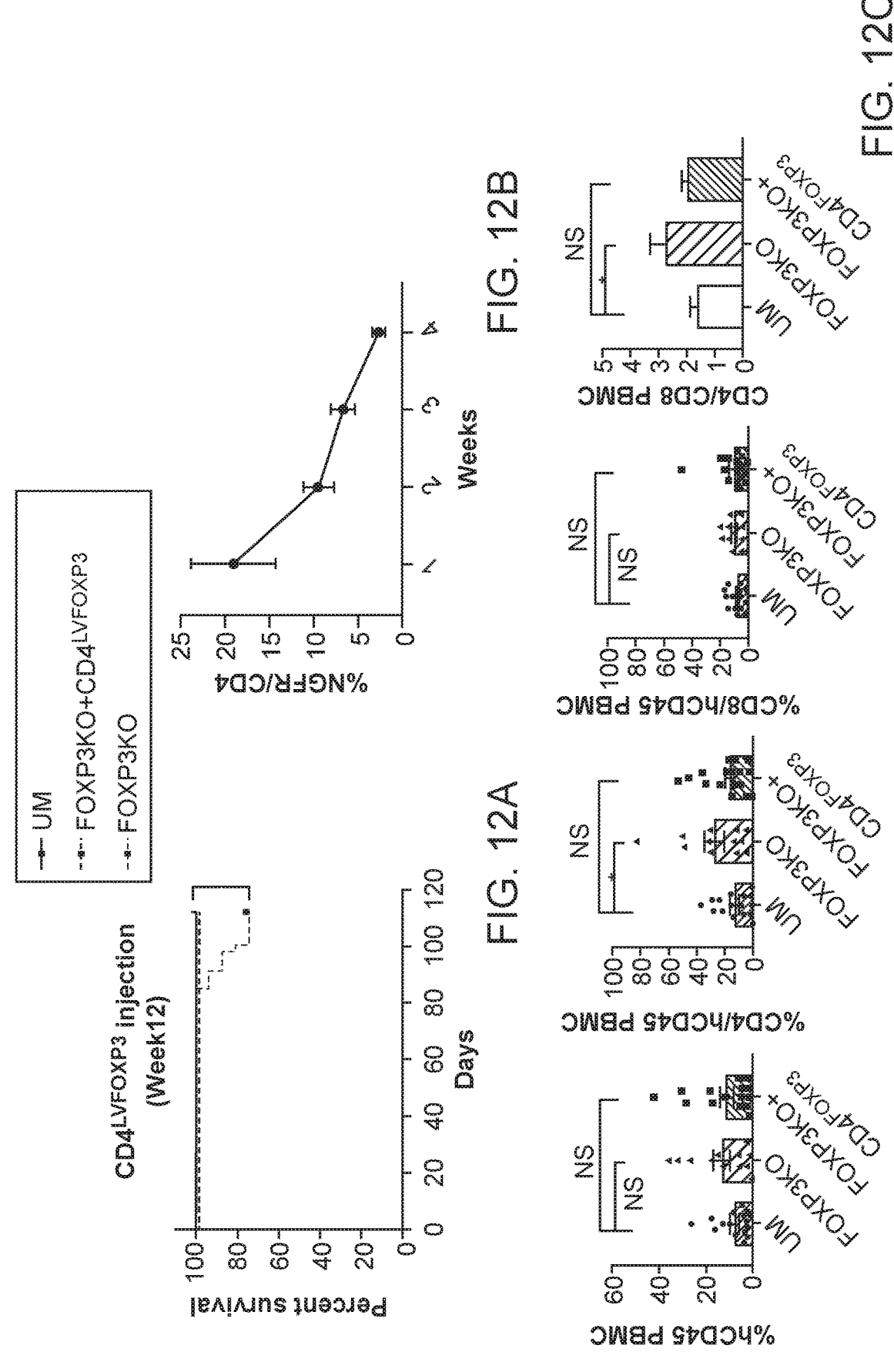

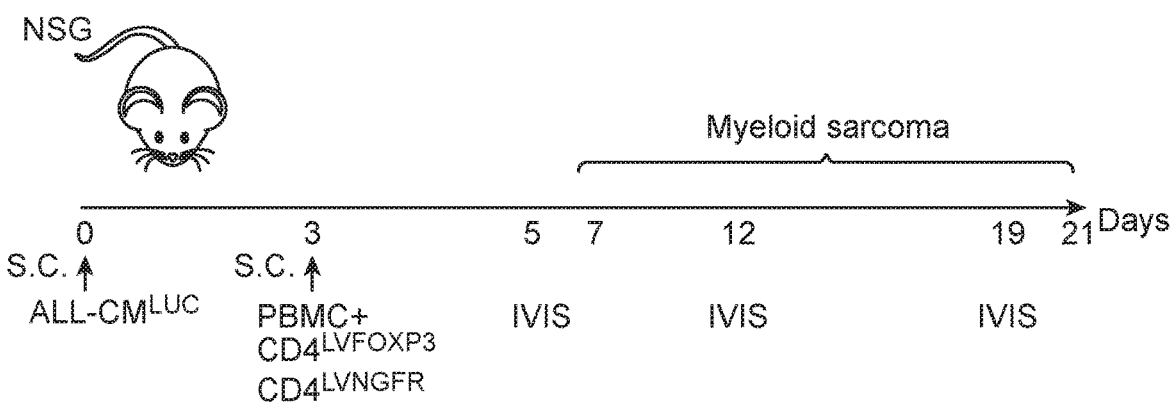
FIG. 14A
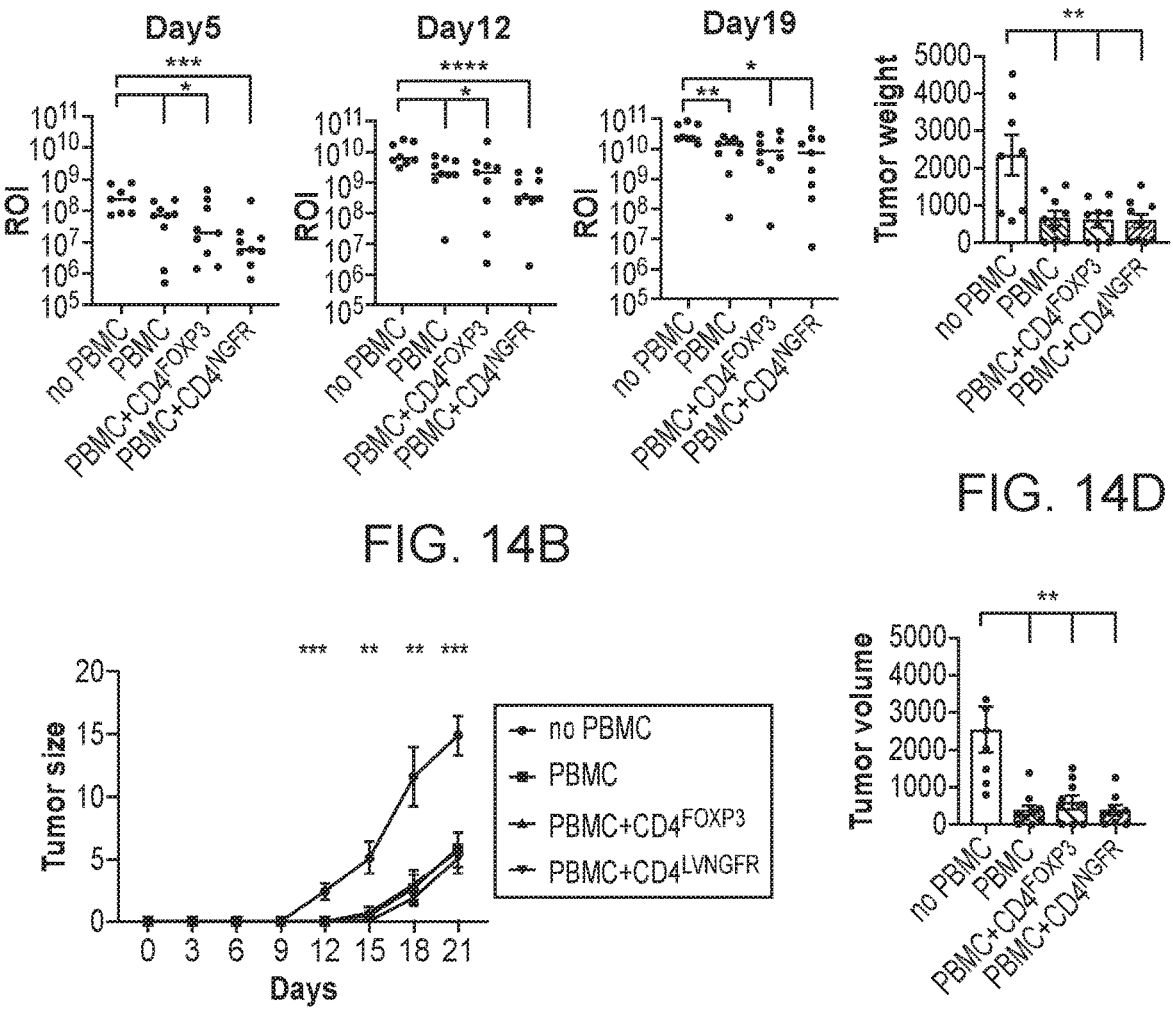
FIG. 14B
FIG. 14D
FIG. 14C
FIG. 14E

FOXP3 ENGINEERED CD4+ T CELLS FOR USE IN TREG-BASED IMMUNOTHERAPY

CROSS REFERENCE

This application claims benefit of U.S. Provisional Patent Application No. 62/858,828, filed Jun. 7, 2019, U.S. Provisional Patent Application No. 62/976,233, filed Feb. 13, 2020, and U.S. Provisional Patent Application No. 62/994, 454, filed Mar. 25, 2020, which applications are incorporated herein by reference in their entirety.

BACKGROUND

Immune regulation, including suppression of autoreactivity, is a fundamental function of a healthy immune system. Regulatory T (Treg) cells actively engage in the maintenance of immunological self-tolerance and immune homeostasis. The transcription factor, Forkhead Box P3 (FOXP3), is the key transcription factor for the function of Treg cells, which are of thymic origin, highly express CD25 and downregulate CD127. Thymic derived Treg cells are strictly dependent on persistent, high FOXP3 expression to exert their suppressive function and modulate immune responses, maintain tolerance to self-antigens and prevent autoimmunity. The occurrence of severe autoimmunity, allergy and immunopathology in humans and rodents with mutated FOXP3 genes demonstrates that deficiency or dysfunction of thymic derived CD4$^+$CD25$^+$Foxp3$^+$ Treg cells alone is sufficient to break self-tolerance in an otherwise normal immune system (reviewed in Bacchetta R. et al., Ann N Y Acad Sci., 2016).

The key role of Treg cells in maintaining tolerance is exemplified by loss-of-function FOXP3 mutations resulting in primary Treg cell dysfunction and the monogenic autoimmune immune dysregulation polyendocrinopathy enteropathy X-linked (IPEX) syndrome (Barzaghi F, et al. Front Immunol., 2012). IPEX syndrome is a deadly X-linked immunodeficiency with severe multiple autoimmune manifestations, most notably in the skin, gastrointestinal tract, and endocrine organs, leading to acute life-threatening or chronic inflammation, lymphoproliferation and autoantibody-mediated pathologies. Without treatment, IPEX is rapidly fatal.

A worldwide survey of the IPEX disease course and the treatment outcomes by collection of data on 96 IPEX patients from multiple centers was performed, including those that are part of the Primary Immune Deficiency Treatment Consortium (PIDTC) and the European Society of Immune Deficiencies Inborn Errors Working Party (ESID-IEWP) (Barzaghi F JACI, 2018). Results from this survey, the largest available for IPEX patients, revealed that 50% of the patients have onset of their disease in the first month of life, while 45% have onset during the first year of life. Only 5% of patients have onset of their disease after the first year, and these cases are usually less severe or atypical. The typical onset is characterized by refractory diarrhea, less often by neonatal type 1 diabetes (T1D) as the first symptom, both associated with severe eczema. However, with disease progression, one out of two patients develop T1D. Usually, IPEX has an acute and devastating onset, which is poorly controlled by pharmacological immunosuppression (IS). During this initial phase of the disease which is the most critical for survival, severe and irreversible organ damage may occur, negatively impacting disease prognosis and treatment outcome. Although rare, the disease has wide geographic distribution and its diagnosis has progressively increased in the past decade, as knowledge of the disease has been disseminated. Although the number of diagnosed patients has increased, advances in therapies for IPEX have not followed.

IPEX patients need prompt therapeutic intervention at onset. The treatment of IPEX syndrome currently relies on nutritional support, replacement therapy for endocrine organ failure, multiple IS drugs, and hematopoietic stem cell transplantation (HSCT). Allogenic HSCT has proven curative, however, it is not available to every patient. Therefore, limited donor availability and the toxicities of allogenic HSCT make this approach less than ideal, especially for patients under 1-year of age. Data from our survey showed that overall survival of IPEX patients after HSCT is 73% with the greatest number of deaths occurring early after transplantation (Barzaghi JACI, 2018). In this same study, the degree of organ impairment at the time of HSCT was the most important variable impacting outcome, independent of age, donor source or conditioning regimen. This strongly supports the importance of stabilizing the patient's clinical condition before HSCT.

Patients not eligible for HSCT, who survive the acute onset period, may stabilize and become more responsive to IS, while this possibility might depend on type of mutation and relative residual protein function. In such cases, patients may reach young adulthood, despite the persistence of disease recurrence, significant organ damage, and new autoimmune manifestations through the years. Indeed, our survey showed that, although the overall survival of patients on chronic IS is not statistically different from that of patients who received HSCT, there was a progressive deterioration of the clinical status of patients receiving IS.

Overall, there is substantial evidence to demonstrate that available treatments are only partially beneficial. Therefore, a therapy aimed specifically at restoring Treg-functions by replacing the dysfunctional Treg cell subsets, targeting the main defect in this rare disease caused by FOXP3 mutations, would address a significant unmet medical need.

IPEX syndrome clinical manifestations recapitulate those occurring in many other autoimmune diseases more commonly observed in the general population. These autoimmune diseases are not due to monogenic defects but rather results from genetic predisposition and environmental co-morbidity factors. Nevertheless, abnormal function or number of Treg cells are involved in their pathogenesis and Treg cell immunotherapy is envisaged as innovative treatment for these diseases (Bluestone J A, Science 2018).

SUMMARY

Engineered CD4$^{LVFOXP3}$ T cells and their use in cellular therapy to promote immune tolerance are provided. In particular, CD4$^{LVFOXP3}$ T cells are produced by transfection of CD4$_+$ T cells with a lentiviral vector expressing FOXP3 under the control of a ubiquitous constitutive promoter, including without limitation the human EF1α promoter. Transduced cells persistently express FOXP3 at high levels and acquire immune suppressive characteristics resembling naturally occurring Treg cells.

In an embodiment, a method of producing CD4$^{LVFOXP3}$ T cells is provided, the method comprising: a) collecting a sample comprising CD4$^+$ T lymphocytes from an individual; b) activating CD4$^+$ T cells, e.g. by polyclonal activation through binding the T cell receptor; c) transducing the CD4$^+$ T lymphocytes with the recombinant lentiviral vector under conditions wherein FOXP3 is constitutively expressed, resulting in conversion of the CD4$^+$ T lymphocytes into regulatory T cell (Treg)-like cells, i.e. $CD4^{LVFOXP3}$ T cells. The cells thus generated find use, for example, in screening assays, therapeutic methods, and the like. FIG. 1 provides an exemplary flow chart.

In another embodiment, a method of adoptive cellular immunotherapy for treating an inflammatory condition is provided, the method comprising: a) collecting a sample comprising $CD4^+$ T lymphocytes from a subject; b) activating $CD4^+$ T cells, e.g. by polyclonal activation through binding the T cell receptor; c) transducing the $CD4^+$ T lymphocytes with the recombinant lentiviral vector under conditions wherein the FOXP3 is constitutively expressed resulting in conversion of the $CD4^+$ T lymphocytes into regulatory T cell (Treg)-like cells, i.e. $CD4^{LVFOXP3}$ T cells; d) purifying by positive isolation the transduced $CD4^{LVFOXP3}$ T cells; e) activating the isolated transduced $CD4^{LVFOXP3}$ T cells e.g. by polyclonal activation through binding the T cell receptor for expansion; and f) administering a therapeutically effective amount of the expanded $CD4^{LVFOXP3}$ T cells to the subject. The biological sample can be any sample comprising $CD4^+$ T lymphocytes, including, for example, without limitation, blood or tissue where $CD4^+$ T lymphocytes are present. In some embodiments, the method further comprises isolating $CD4^+$ T lymphocytes from the biological sample.

The biological sample can be any sample comprising $CD4^+$ T lymphocytes, including, for example, without limitation, blood or tissue where $CD4^+$ T lymphocytes are present. $CD4^+$ T lymphocyte populations may comprise naïve T cells, memory T cells, total T cells; etc. In some embodiments, the method further comprises isolating $CD4^+$ T lymphocytes from the biological sample.

In certain embodiments, the method further comprises substantially purifying the $CD4^{LVFOXP3}$ T cells. In some embodiments, the $CD4^{LVFOXP3}$ T cells are substantially purified by positive selection for the cell surface marker encoded by the recombinant lentiviral vector. For example, if the cell surface marker is a truncated nerve growth factor receptor (tNGFR), the $CD4^{LVFOXP3}$ T cells can be substantially purified by positive selection for the tNGFR cell surface marker using for example, without limitation, immunomagnetic separation or flow cytometry. Alternatively, to enrich for transduced cells the culture is maintained in the presence of a concentration of rapamycin effective to reduce the number of non-transduced cells.

In certain embodiments, the method further comprises culturing the $CD4^+$ T lymphocytes during and after transduction. In some embodiments, the method of claim further comprises adding IL-2 and IL-7 to a culture of $CD4^+$ T lymphocytes to expand the number of $CD4^+$ T lymphocytes in the culture.

In certain embodiments, the method further comprises culturing the $CD4^{LVFOXP3}$ T cells. In some embodiments, the method further comprises adding IL-2 and IL-15 to a culture of $CD4^{LVFOXP3}$ T cells to expand the number of $CD4^{LVFOXP3}$ T cells in the culture.

In certain embodiments, the method further comprises inducing or isolating a subpopulation of T lymphocytes comprising a T cell receptor specific for an antigen of interest such as, an alloantigen, an autoantigen, or an allergen, and transducing as described herein to generate a population of antigen-specific $CD4^{LVFOXP3}$ T cells.

In one aspect, a bidirectional lentiviral vector of not more than about 11,000 bp, usually not more than about 10,500 bp and may not more than about 10,100 bp, comprising full-length FOXP3 cDNA expressed under an EF1α promoter and NGFR expressed under the minimal CMV promoter from the opposite strand is utilized. The vector may comprise each of: a) a polynucleotide encoding forkhead box protein 3 (FOXP3), conferring to the $CD4^+$ T lymphocytes specific regulatory function; b) an elongation factor 1a (EF1α) promoter, wherein the EF1α promoter is operably linked to the polynucleotide encoding FOXP3; c) a polynucleotide encoding a cell surface marker for tracking and selection of cells transfected with the vector; d) a mutated Woodchuck hepatitis virus posttranscriptional regulatory element (WPRE) modified to remove a WHx start codon; e) human immunodeficiency virus (HIV)-derived elements comprising a 5' long terminal repeat (5' LTR), a Ψ packaging signal, a truncated Gag sequence, a rev response element (RRE) sequence, a central polypurine tract (cPPT), a central termination sequence (CTS), a truncated negative regulatory factor (NEF) sequence, and a partially deleted and self-inactivated (SIN) 3' long terminal repeat (3' LTR); f) a polyadenylation sequence; g) an SV40 origin of replication; h) a bacterial high copy origin of replication (Ori) and (i) kanamycin resistance gene. In one embodiment, the cell surface marker is a truncated nerve growth factor receptor (tNGFR). An exemplary lentiviral expression vector comprises the components arranged as depicted in the vector map shown in FIG. 2, or as set out in Table 2. In one embodiment, the recombinant lentiviral vector comprises the nucleotide sequence of SEQ ID NO:2 or a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the recombinant lentiviral vector is capable of generating a $CD4^{LVFOXP3}$ T cells by transduction of a $CD4^+$ T lymphocyte. The $CD4^{LVFOXP3}$ T cells produced by this method are Treg-like cells called $CD4^{LVFOXP3}$ T cells.

In certain embodiments, the method further comprises transducing the $CD4^+$ T lymphocytes with a recombinant polynucleotide encoding an exogenous T cell receptor or a chimeric antigen receptor (CAR). In other embodiments, the method further comprises culturing the transduced Treg-like lymphocytes to increase expression of homing receptors, e.g. increasing expression of receptor that provide for enhanced migration to the intestinal mucosa, which requires the expression of very specific homing receptors on T cells, integrin α4β7 and chemokine receptor CCR9.

In another aspect, $CD4^{LVFOXP3}$ T cells produced by the methods described herein are provided. In another aspect, a composition comprising $CD4^{LVFOXP3}$ T cells for use in treatment of an inflammatory condition is provided. In some embodiments, a composition of $CD4^{LVFOXP3}$ T cells is substantially purified free of other cells. In some embodiments, the composition further comprises a pharmaceutically acceptable excipient. In another embodiment, a composition comprising a $CD4^{LVFOXP3}$ T cell for use in treatment of IPEX syndrome is provided.

In another aspect, a method of treating an inflammatory, e.g. an autoimmune, condition in a subject is provided, the method comprising administering a therapeutically effective amount of a composition comprising $CD4^{LVFOXP3}$ T cells to the subject. The composition is generally administered in an amount sufficient to reduce inflammation in the subject. In certain embodiments, multiple cycles of treatment are administered to the subject.

In certain embodiments, the $CD4^+$ T lymphocytes, from which the $CD4^{LVFOXP3}$ T cells are derived (i.e., by transduction with a lentiviral vector expressing FOXP3 as described herein), are autologous or allogeneic.

In certain embodiments, the method further comprises activating the CD4$^+$ T lymphocytes before transduction. In some embodiments, the method further comprises adding IL-2 and IL-15 to a culture of CD4$^+$ T lymphocytes to expand the number of CD4$^+$ T lymphocytes in the culture. Culturing may be performed in vitro or ex vivo.

In certain embodiments, the method further comprises culturing the CD4$^{LVFOXP3}$ T cells before administration to a subject. In some embodiments, the method further comprises adding IL-2 and IL-15 to a culture of CD4$^{LVFOXP3}$ T cells to expand the number of CD4$^{LVFOXP3}$ T cells in the culture. Culturing may be performed in vitro or ex vivo.

The methods described herein can be used to treat inflammatory conditions, including for example, without limitation, Treg deficiency, autoimmune disorders, allergies, acute inflammatory syndromes, graft-versus-host disease, and transplant rejection. In one embodiment, the Treg deficiency/autoimmune disorder is IPEX syndrome. In another embodiment, the method is performed prior to performance of a tissue or organ transplant, in conjunction with a tissue or organ transplant, or after a tissue or organ transplant.

In another embodiment, a method of treating immune dysregulation polyendocrinopathy enteropathy X-linked (IPEX) syndrome is provided, the method comprising administering a therapeutically effective amount of a composition comprising CD4$^{LVFOXP3}$ T cells to the subject, as described herein.

CD4$^{LVFOXP3}$ T cells may be administered by any suitable mode of administration. In some embodiments, the CD4$^{LVFOXP3}$ T cells are administered intravenously or intra-arterially. In another embodiment, the CD4$^{LVFOXP3}$ T cells are administered locally at a site of inflammation. In another embodiment, the CD4$^{LVFOXP3}$ T cells are administered locally at a site of a tissue or organ transplant.

In one embodiment, an animal model for FOXP3 deficiency is provided. In such an animal model, FOXP3 deficient CD34$^+$ hematopoietic stem and progenitor cells (HSPCs) from a human donor are transplanted intrahepatically in neonatal pups, e.g. of about 3-5 days old, of immune deficient mice. Suitable mouse strains include, for example, NSG mice, SGM3_NSG mice, etc. that lack mature T cells, B cells, and functional NK cells, and are deficient in mouse cytokine signaling. The FOXP3 deficient CD34$^+$ HSPCs can be obtained from a human donor that is deficient in FOXP3, e.g. an IPEX patient; or alternatively obtained from an individual with normal FOXP3 expression, where the HSPCs are genetically manipulated in vitro to reduce FOXP3 expression, e.g. by targeting FOXP3 with a CRISPR-Cas9 RNP construct. The resulting animal model has human immune system cells deficient in FOXP3 expression.

The efficacy of engineered CD4$^{LVFOXP3}$ T cells in preventing and controlling lymphoproliferation of FOXP3 deficient CD4$^+$ T cells can be determined by administering such engineered cells to the mouse model described above and determining the effect on lymphoproliferation.

The safety and/or efficacy of engineered CD4$^{LVFOXP3}$ T cells in completion and expansion of an immune response to pathogens, including but not limited to fungi, e.g. *Candida albicans*; virus. e.g. adenovirus; protozoan pathogens, bacterial pathogens, etc. can be determined by administering such engineered cells to the immune deficient mouse model mentioned above in combination with human T cells primed with a pathogen, and determining the effect of the engineered cells on the immune response.

The safety and/or efficacy of engineered CD4$^{LVFOXP3}$ T cells in immune surveillance and tumor clearance can be determined by administering such engineered cells to the immune deficient mouse model mentioned above in combination with a tumor xenograft, e.g. skin sarcoma, and determining the effect of the engineered cells on the ability of human peripheral blood mononuclear cells (PBMC) to develop an immune response and clear the tumor.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1 shows a process flow chart for CD4$^{LVFOXP3}$ production.

FIG. 8 shows that both CD4$^{LVFOXP3}$ autologous or allogeneic to the responder T cells can efficiently prevent xenoGvHD. The experimental design (a) and results from one representative experiment are shown (b). Autologous and allogeneic CD4$^{LVFOXP3}$ generated in parallel were co-injected with effector CD4$^+$ T cells. CD4$^{LVFOXP3}$ autologous or allogeneic showed similar engraftment and in vivo survival. Percentage engraftment of total CD45+ human cells (c) and of NGFR+ transduced cells (d) is higher when CD4$^{LVFOXP3}$ are autologous to the effector cells.

FIG. 14 shows the experimental design (a) and the results of the experiment assessing the impact of CD4$^{LVFOXP3}$ on tumor clearance by normal PBMC (b-e). Clearly, the tumor size increased only in the control mice that were not injected with PBMC, while it was reduced in the mice injected with PBMC as well as in the mice injected with PBMC+ CD4$^{LVFOXP3}$ indicating that the transduced cells did not impair tumor clearance.

DETAILED DESCRIPTION OF EMBODIMENTS

Figure 2A:
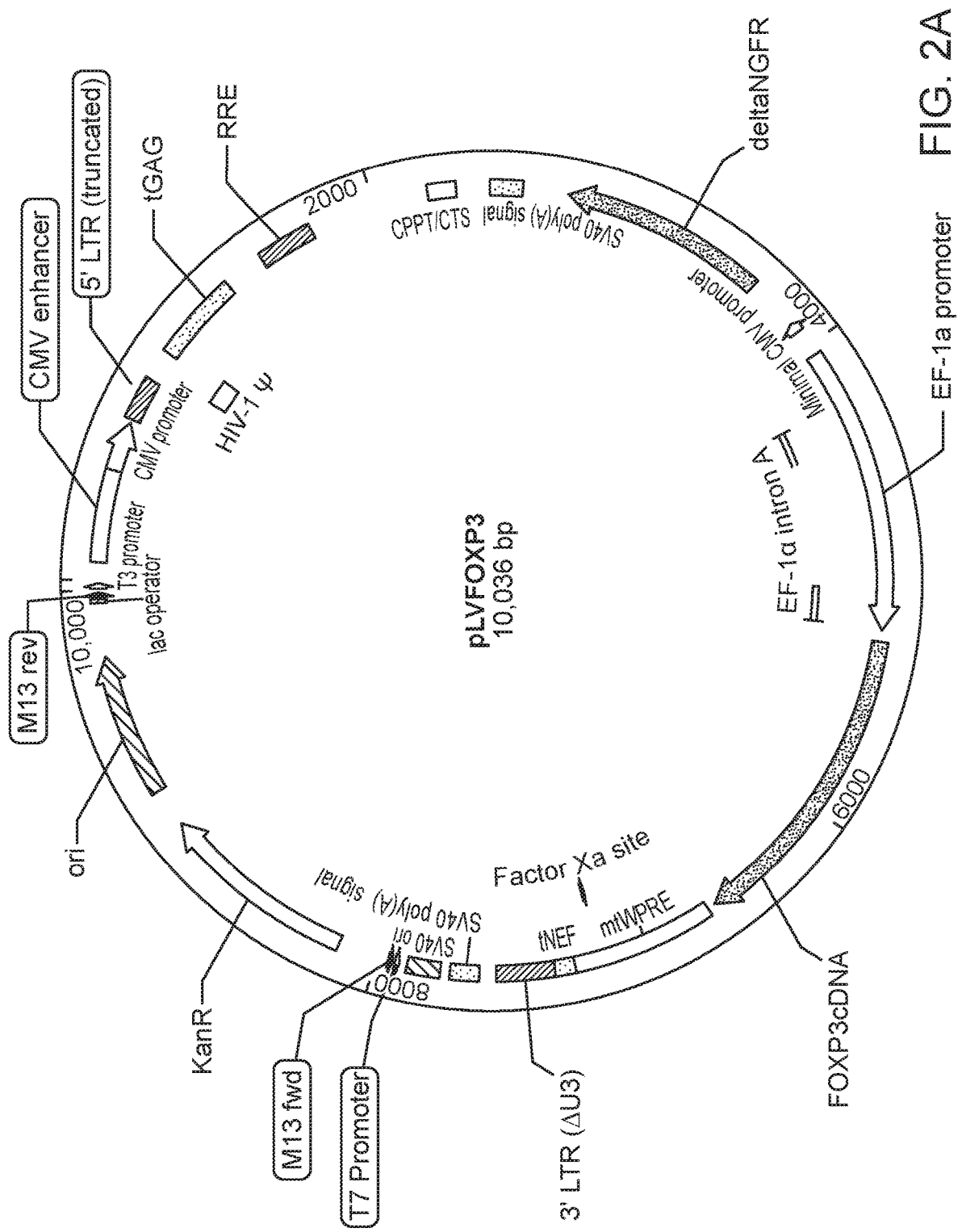
FIG. 2. A. shows the LVFOXP3 Transfer Plasmid Map. The map shows all components of the 10,036 bp transfer plasmid pLVFOXP3 used for vector production by transient transfection of HEK293T cells. B. LVFOXP3 Transfer Plasmid Component Descriptions.

Engineered CD4$^{LVFOXP3}$ T cells and their use in cellular therapy to promote immune tolerance are disclosed. In particular, CD4$^{LVFOXP3}$ T cells are produced by transduction of CD4$^+$ T cells with a lentiviral vector expressing FOXP3 under the control of a constitutive promoter. Transduced cells express FOXP3 at high and persistent levels and acquire immune phenotypic and immune suppressive characteristics resembling naturally occurring Treg cells. Methods of preclinical assessments of efficacy and safety of the CD4$^{LVFOXP3}$ T cells and methods of using such CD4$^{LVFOXP3}$ T cells in cellular therapy for treating various inflammatory conditions benefitting from increased immune tolerance, such as IPEX syndrome, as well as other conditions associated with Treg deficiency of different origin, inflammation, and/or immune dysregulation such as autoimmune diseases, graft-versus-host disease, transplant rejection, and allergies are also provided.

Before the engineered CD4$^{LVFOXP3}$ T cells and their use in treatment of inflammatory conditions are further described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the regulatory T cell-like cells" includes reference to one or more regulatory T cell-like cells and equivalents thereof, e.g. $CD4^{LVFOXP3}$ cells, Treg-like cells, or engineered Tregs, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

"Immune tolerance", or "tolerogenic" refers to cells capable of suppressing or down-modulating an adaptive or innate immunological response.

The term "biological sample" encompasses a clinical sample. The types of "biological samples" include, but are not limited to: tissue obtained by surgical resection, tissue obtained by biopsy, cells in culture, cell supernatants, cell lysates, tissue samples, organs, bone marrow, blood, plasma, serum, fine needle aspirate, lymph node aspirate, cystic aspirate, a paracentesis sample, a thoracentesis sample, and the like.

The terms "obtained" or "obtaining" as used herein can also include the physical extraction or isolation of a biological sample (e.g., comprising CD4$^+$ T lymphocytes) from a subject. Accordingly, a biological sample comprising CD4$^+$ T lymphocytes can be isolated from a subject (and thus "obtained") by the same person or same entity that subsequently isolates CD4$^+$ T lymphocytes from the sample and produces $CD4^{LVFOXP3}$ T cells (transduced with a lentiviral vector expressing FOXP3) from the original unmodified CD4$^+$ T lymphocytes in the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a biopsy sample, an aspirate, etc.) will be known to one of ordinary skill in the art and any convenient method may be used to isolate a biological sample.

"Substantially purified" generally refers to isolation of a component of a sample (e.g., cell or substance), such that the component comprises the majority percent of the sample in which it resides. Typically, in a sample, a substantially purified component comprises at least 70%, preferably at least 80%-85%, more preferably at least 90-99% of the sample.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). In terms of clinical trials for evaluation of safety, efficacy may not be a primary endpoint, but rather lack of toxicity may be considered treatment. Those in need of treatment include those already inflicted as well as those in which prevention is desired (e.g., those with increased susceptibility to an autoimmune disease, etc.)

A therapeutic treatment includes one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

An "effective amount" of a composition comprising $CD4^{LVFOXP3}$ T cells (i.e., CD4$^+$ T lymphocytes transfected with a lentiviral vector expressing FOXP3) is an amount sufficient to safely effect beneficial or desired results, such as an amount that suppresses activation and proliferation of effector T cells and increases immune tolerance. An effective amount can be administered in one or more administrations, applications, or dosages.

By "therapeutically effective dose or amount" of a composition comprising $CD4^{LVFOXP3}$ T cells (i.e., $CD4^+$ T lymphocytes transfected with a lentiviral vector expressing FOXP3) is intended an amount that, when administered as described herein, brings about a positive therapeutic response, such as improved recovery from an inflammatory condition such as, but not limited to, an autoimmune manifestation, an allergy, an acute inflammatory response, graft-versus-host disease, and transplant rejection. Improved recovery may include a reduction in inflammation, pain, or autoimmune-induced tissue damage, or better graft tolerance and prolonged survival of transplanted cells, tissue or organs. Improved recovery may include an improvement towards normalization of parameters such as ALC or specific cell subsets, eosinophils, CRP, cytokines in plasma, markers of specific organ function, Ab levels, and the like. Additionally, a therapeutically effective dose or amount may compensate for functional (e.g., IPEX syndrome) or quantitative Treg-deficiency and reduce the need for immunosuppressive or anti-inflammatory drugs. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein. For example, an effective unit dose may be $10^6$ $CD4^{LVFOXP3}$ T cells/kg, $3×10^6$ $CD4^{LVFOXP3}$ T cells/kg, $10^7$ $CD4^{LVFOXP3}$ T cells/kg, $10^8$ $CD4^{LVFOXP3}$ T cells/kg, $10^9$ $CD4^{LVFOXP3}$ T cells/kg, or more.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome. The term "isolated" when referring to a cell, is a cell that is separate and discrete from the whole organism with which the cell is found in nature.

"Substantially purified" generally refers to isolation of a substance (compound, drug, polynucleotide, protein, polypeptide) such that the substance comprises the majority percent of the sample in which it resides. Typically in a sample, a substantially purified component comprises 50%, preferably 80%-85%, more preferably 90-95% of the sample. Techniques for purifying substances of interest are well-known in the art and include, for example, ion-exchange chromatography, affinity chromatography and sedimentation according to density.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

The term "unit dosage form," as used herein, refers to physically discrete units suitable as unitary dosages for human and animal subjects, each unit containing a predetermined quantity of the agents calculated in an amount sufficient to produce the desired effect in association with a pharmaceutically acceptable diluent, carrier or vehicle. The specifications for the unit dosage forms for use in the present invention depend on the particular compound employed and the effect to be achieved, the pharmacodynamics associated with each compound in the host, and the like.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome. Transduction, where an exogenous polynucleotide is integrated into the host genome, i.e. the T lymphocyte genome, is preferred for the methods described herein.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant" refers to biologically active derivatives of the reference molecule that retain desired activity. In general, the term "variant" refers to molecules having a native sequence and structure with one or more additions, substitutions (generally conservative in nature) and/or deletions, relative to the native molecule, so long as the modifications do not destroy biological activity, and which are "substantially homologous" to the reference molecule. In general, the sequences of such variants will have a high degree of sequence homology to the reference sequence, e.g., sequence homology of more than 50%, generally more than 60%-70%, even more particularly 80%-85% or more, such as at least 90%-95% or more, when the two sequences are aligned.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

Engineered Treg-Like Cells, CD4$^{LVFOXP3}$ T cells.

Compositions, methods, and kits are provided for producing and using engineered CD4$^{LVFOXP3}$ T cells expressing FOXP3. FOXP3 is a transcription factor essential for the function of natural Tregs in maintenance of immune tolerance. Lentivirus-mediated expression of FOXP3 in CD4$^+$ T lymphocytes endows cells with Treg-like characteristics, including the ability to suppress immune responses of effector T cells and other immune cells. CD4$^{LVFOXP3}$ T cells are useful for increasing immune tolerance to antigens in a subject such as alloantigens, autoantigens, and allergens. Accordingly, pharmaceutical compositions comprising such engineered CD4$^{LVFOXP3}$ T cells are useful for treating inflammatory and immune dysregulatory conditions benefitting from increased immunological tolerance, including, but not limited to, Treg deficiency, autoimmune diseases, allergies, graft-versus-host disease, and transplant rejection.

CD4$^{LVFOXP3}$ can be obtained from total CD4$^+$ T cells, requiring only limited CD4$^{LVFOXP3}$ in vitro expansion with cytokines, for example up to 5 to 10-fold expansion in a 2-3-week-culture.

In the process of generating clinically acceptable CD4$^{LVFOXP3}$, patient CD4$^+$ T cells are isolated from a biological sample, e.g. from non-mobilized apheresis product. The CD4$^+$ T cells are genetically modified in vitro by lentiviral-mediated gene transfer with the recombinant lentiviral vector LVFOXP3.

In some embodiments, CD4$^+$ T cells are isolated from non-mobilized apheresis by immunomagnetic separation using cGMP compliant reagents and device. The isolated CD4$^+$ T cells are cultured for up to 24 hours in medium comprising IL-2 at a concentration of from about 10 to about 1000 U/ml, and may be from about 50 to about 500 U/ml, e.g. from about 75 to about 150 U/ml; and IL-7 at a concentration of from about 0.5 to about 500 ng/ml, and may be from about 1 to about 100 ng/ml, e.g. from about 5 to about 50 ng/ml. Following transduction on Day 1, the transduced cells are cultured in medium comprising IL-2 at a concentration of from about 10 to about 1000 U/ml, and may be from about 50 to about 500 U/ml, e.g. from about 75 to about 150 U/ml; and IL-15 at a concentration of from about 0.5 to about 500 ng/ml, and may be from about 1 to about 100 ng/ml, e.g. from about 5 to about 50 ng/ml for a period of from 5 to 15 days, e.g. from 6 to 12 days, for example from 6 to 8 days. The transduced CD4$^+$ T cells are then selected for expression of a marker from the vector, including without limitation NGFR. Selection may utilize magnetic microbead. Post-selection, cells are cultured in in the IL-2/IL-15 medium as described above. The transduced selected CD4+ cells may be re-stimulated by the addition of an agent that binds to and activates polycloncal T cell receptor, e.g. anti-CD3; MACS® GMP T Cell TransAct™; etc. The expanded cells are harvested between about day 16 to 21.

CD4$^{LVFOXP3}$ T cells express high and stable levels of CD25 on the membrane that is directly regulated by FOXP3. As a safety measure, these cells can be eliminated in vivo by administration of an anti-CD25 mAb, including without limitation the commercially available antibody Basiliximab, which is approved for in use in pediatric and adult patients undergoing transplantation.

Conversion of CD4$^+$ T Lymphocytes into CD4$^{LVFOXP3}$ T Cells

A recombinant lentiviral vector comprising a FOXP3 gene under the control of a constitutive promoter is used to convert CD4$^+$ T lymphocytes into CD4$^{LVFOXP3}$ T cells. For example, nucleic acids encoding the forkhead box protein 3 (FOXP3) transcription factor can be inserted into the lentivirus vector to create an expression cassette capable of expressing the FOXP3 in a suitable host CD4$^+$ T lymphocyte.

In some embodiments, the recombinant lentiviral vector comprises: a) a polynucleotide encoding forkhead box protein 3 (FOXP3); b) an elongation factor 1a (EF1α) promoter, wherein the EF1α promoter is operably linked to the polynucleotide encoding FOXP3; c) a polynucleotide encoding a cell surface marker for in vitro selection and in vivo tracking of cells transduced with the vector; d) a modified Woodchuck hepatitis virus posttranscriptional regulatory element (WPRE) modified to remove a WHx start codon; e) human immunodeficiency virus (HIV)-derived elements comprising a 5' long terminal repeat (5' LTR), a Ψ packaging signal, a truncated Gag sequence, a rev response element (RRE) sequence, a central polypurine tract (cPPT), a central termination sequence (CTS), a truncated negative regulatory factor (NEF) sequence, and a 3' long terminal repeat (5' LTR); f) a polyadenylation sequence; g) an SV40 origin of replication; and h) a bacterial high copy origin of replication (Ori).

Figure 1:
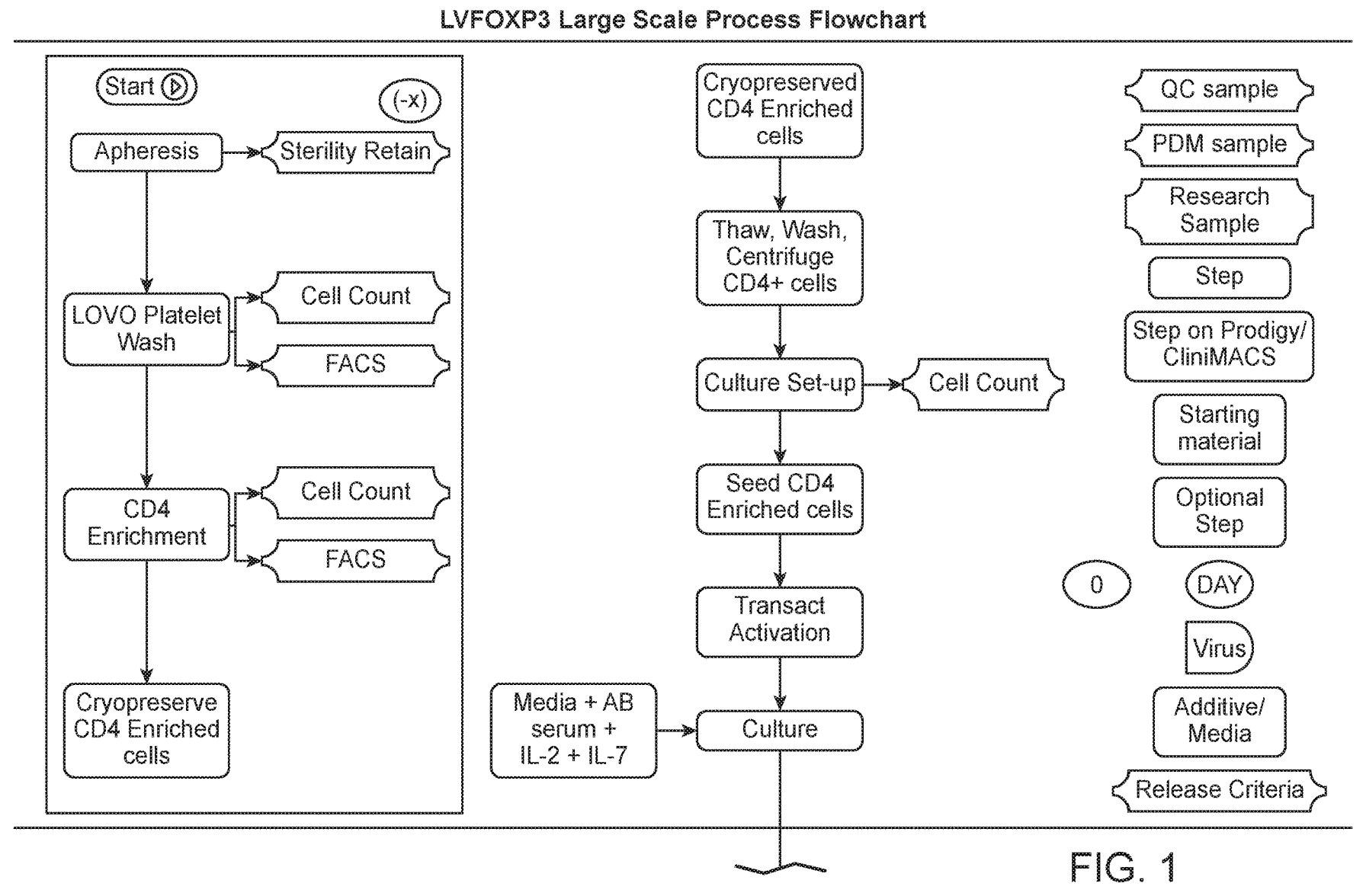

In one embodiment, the cell surface marker is a truncated nerve growth factor receptor (NGFR). In another embodiment, the recombinant lentiviral vector further comprises a CMV promoter operably linked to the polynucleotide encoding the NEF. An exemplary lentiviral expression vector comprises the components arranged as depicted in the vector map shown in FIG. 1. In one embodiment, the recombinant lentiviral vector comprises the nucleotide sequence of SEQ ID NO:2 or a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the recombinant lentiviral vector is capable of generating a Treg-like cell by transfection of a CD4$^+$ T lymphocyte.

The ability of constructs to produce FOXP3 can be empirically determined, for example, by using a real-time RT-PCR assay of FOXP3 mRNA levels or a Western Blot assay of FOXP3 protein levels. Additionally, the ability of the lentiviral vector to confer Treg-like characteristics on CD4$^+$ T lymphocytes can be evaluated with a suppression assay in vitro (see Examples).

FOXP3 nucleic acid and protein sequences may be derived from any source. A number of FOXP3 nucleic acid and protein sequences are known. A representative example of a human FOXP3 gene sequence is presented in SEQ ID NO:1 and additional representative sequences including various isoforms of the FOXP3 transcription factor are listed in the National Center for Biotechnology Information (NCBI) database. See, for example, NCBI entries: Accession Nos. NM_001114377, NM_014009, NG_007392, XM_006724533, XM_017029567, NP_001107849, NP_054728, XP_016885056, and XP_006724596; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a lentiviral construct, wherein the expressed variant FOXP3 retains biological activity, including transcription factor activity and the ability to convert CD4$^+$ T lymphocytes into CD4$^{LVFOXP3}$ T cells.

The CD4$^+$ T lymphocytes can optionally be purified before or after transduction by any method known in the art, including, but not limited to, density gradient centrifugation (e.g., Ficoll Hypaque, percoll, iodoxanol and sodium metrizoate), immunoselection (positive selection or negative selection for surface markers) with immunomagnetic beads or immunoaffinity columns, or fluorescence-activated cell sorting (FACS). For example, CD4$^+$ T lymphocytes can be isolated from apheresis products by immunomagnetic CD4$^+$ cell selection, cultured in the presence of IL-2 and IL-7, then activated and transduced with the lentiviral vector, followed by immunoselection for the cell surface marker (e.g., truncated NGFR) expressed by the recombinant lentiviral vector to separate transduced CD4$^{LVFOXP3}$ T cells from non-transduced T cells (see, Examples). The resulting cells may be restimulated and cultured in the presence of IL-2 and IL-15.

The ability of the engineered CD4$^{LVFOXP3}$ T cells to suppress proliferation and activation of effector T cells and other immune cells can be assayed by methods well known in the art including, for example, without limitation, performing an in vitro suppression assay or $^3$H-thymidine assay that measures suppression of T cell proliferation by CD4$^{LVFOXP3}$ T cells, or a flow cytometry-based suppression assay that measures suppression of proliferation and cytokine production in subpopulations of T cells and other immune cells (see, e.g., Thornton et al. (1998) J. Exp. Med. 1998. 188:287-296, Schneider et al. (2011) Methods Mol. Biol. 707:233-241, Baecher-Allan et al. (2005) Clin. Immunol. 115:10-18, McMurchy et al. (2012) Eur. J. Immunol. 42:27-34; herein incorporated by reference.

Antigen Specificity

In some embodiments, antigen-specific Treg therapy is performed with CD4$^{LVFOXP3}$ T cells expressing a T cell receptor specific for a particular antigen of interest, wherein the Treg induces immunological tolerance selectively to the antigen of interest. The use of antigen-specific Tregs avoids the risk of general immunosuppression. In certain embodiments, the antigen specificity of a Treg is controlled by introducing an exogenous T cell receptor having specificity for an antigen of interest into a Treg. For example, Tregs can be transduced with a viral vector encoding a natural T cell receptor or an artificial T cell receptor such as a chimeric antigen receptor (CAR) having the desired specificity for an antigen of interest. CARs are artificial T cell receptors that typically comprise a single-chain variable fragment (scFv), which provides antigen specificity, fused to a T cell co-stimulatory domain and an activation domain. CARs can recognize epitopes of a target antigen of interest expressed on a cell surface (e.g., B cells or antigen presenting cells), but are not MHC-restricted. In CD4$^{LVFOXP3}$ T cells, designed with exogenous T cell receptors (e.g., natural or artificial) specific for an antigen of interest, the gene for the endogenous T cell receptor may be inactivated or deleted. For a review of engineering antigen-specific Tregs with exogenous T cell receptors and CAR receptors, see, e.g., Dawson et al. (2017) Transl. Res. 187:53-58, Boardman et al. (2016) Biochem. Soc. Trans. 44(2):342-8, Adair et al. (2017) Front. Immunol. 8:1117, Zhang et al. (2018) Front. Immunol. 2018; 9: 2359, Tsang et al. (2008) J. Clin. Invest. 118(11):3619-28, Kim et al. (2015) Blood 125(7):1107-15, Brusko et al. (2010) PLoS One 5(7):e11726, Wright et al. (2009) Proc. Natl. Acad. Sci. U.S.A. 106(45):19078-83, Schubert et al. (2018) Int. J. Cancer. 142(9):1738-1747; herein incorporated by reference.

CD4$^+$ T lymphocytes may be obtained from a biological sample collected from either healthy individuals or patients with an inflammatory and immune dysregulatory condition (e.g., Treg deficiency/autoimmune disease such as IPEX syndrome). The biological sample may be any sample containing CD4$^+$ T lymphocytes, such as a blood sample, a sample of peripheral blood mononuclear cells (PBMCs), or inflamed tissue in which the CD4$^+$ T lymphocytes have infiltrated. CD4$^+$ T lymphocytes can be isolated from a bodily fluid (e.g., blood) or tissue and cultured prior to gene transfer with a recombinant lentiviral vector expressing FOXP3 to generate CD4$^{LVFOXP3}$ T cells. Culture media may be supplemented with interleukin 2 (IL-2) and IL-7 to expand the numbers of cells before and/or after transduction.

In some embodiments, antigen-specific CD4$^+$ T lymphocytes are obtained by eliciting an immune response to an antigen of interest. CD4$^+$ T lymphocytes may be contacted with an antigen of interest (in the presence of an antigen presenting cell) in vivo, ex vivo, or in vitro. For example, the antigen of interest can be administered to a subject to elicit a CD4$^+$ T cell response followed by collection of a biological sample from the subject comprising T cells recognizing the antigen of interest. The biological sample may be any sample containing CD4$^+$ T lymphocytes specific for the antigen of interest, such as a blood sample, a sample of peripheral blood mononuclear cells (PBMCs), or inflamed tissue in which antigen-specific CD4$^+$ T lymphocytes have infiltrated. Alternatively, a biological sample comprising CD4$^+$ T lymphocytes can be collected from a subject and treated with an antigen of interest in the presence of an antigen-presenting cell ex vivo or in vitro. Such induced antigen-specific CD4$^+$ T lymphocytes can be at the same time transduced with a recombinant lentiviral vector expressing FOXP3 and if desired a marker gene of interest, to generate antigen-specific CD4$^{LVFOXP3}$ T cells. Antigens of interest may include, for example, alloantigen or autoantigen specific for an autoimmune disease of interest.

Examples of suitable antigen presenting cells that can present an antigen of interest to CD4$^+$ T lymphocytes include dendritic cells, macrophages, and activated B cells. Alternately, artificial antigen presenting cells may be used, such as soluble major histocompatibility complex (MHC)-multimers or cellular or acellular artificial antigen presenting cells. MHC-multimers typically range in size from dimers to octamers (tetramers commonly used) and can be used to display class 1 or class 2 MHC (Hadrup et al. (2009) Nature Methods 6:520-526, Nepom et al. (2003) Antigen 106:1-4, Bakker et al. (2005) Current Opinion in Immunology 17:428-433). Cellular artificial antigen presenting cells may include cells that have been genetically modified to express T-cell co-stimulatory molecules, MHC alleles and/or cytokines. For example, artificial antigen presenting cells have been generated from fibroblasts modified to express HLA molecules, the co-stimulatory signal, B7.1, and the cell adhesion molecules, ICAM-1 and LFA-3 (Latouche et al. (2000) Nature Biotechnology. 18 (4):405-409). Acellular antigen presenting cells comprise biocompatible particles such as microparticles or nanoparticles that carry T cell activating proteins on their surface (Sunshine et al. (2014) Biomaterials. 35 (1): 269-277), Perica et al. (2014) Nanomedicine: Nanotechnology, Biology and Medicine. 10 (1): 119-129). For a review of artificial antigen presenting cells, see, e.g., Oelke et al. (2004) Clin. Immunol. 110(3):243-251, Wang et al. (2017) Theranostics 7(14):3504-3516, Butler et al. (2014) Immunol Rev. 257(1):191-209, Eggermont et al. (2014) Trends Biotechnol. 32(9):4564-4565, Sunshine et al. (2013) Nanomedicine (Lond) 8(7):1173-1189, and Rhodes et al. (2018) Mol. Immunol. 98:13-18; herein incorporated by reference.

Typically, the antigen of interest is at a concentration ranging from about 10 μg/ml to about 40 μg/ml in the biological sample. The antigen of interest may be pre-incubated with the antigen presenting cells for periods ranging from 1 to 18 hours prior to stimulation of the CD4$^+$ T lymphocytes. Culture media may be supplemented with interleukin 2 (IL-2) and interleukin 15 (IL-15) during intervals between stimulations to induce amino acid uptake and protein synthesis in antigen-activated T cells to promote growth and proliferation of antigen-specific CD4$^+$ T lymphocytes. The antigen-specific CD4$^+$ T lymphocytes can subsequently be isolated from biological samples and transduced with a lentiviral vector expressing FOXP3, as described herein.

The cells may additionally be cultured with agents during Treg expansion that enhance expression of specific homing receptors. For example, culture in the presence of IFNγ and IL12 can enhance expression of CXCR3. Addition of retinoic acid (RA) during Treg expansion can induce expression of the gut-homing receptors α4β7-integrin and CCR9. See, for example, Hoeppli et al. (2019) Am J Transplant. 19(1):62-76.

Applications

The methods described herein are useful for treating various immune conditions and disorders benefitting from increased immunological tolerance, such as inflammatory conditions including for example, without limitation, Treg deficiency, autoimmune disorders, allergies, acute inflammatory syndromes, graft-versus-host disease, and organ or tissue transplantation. In some embodiments, polyclonal CD4$^{LVFOXP3}$ T cells comprising a plurality of different T cell receptors are used for immunosuppression and promoting immune tolerance generally. In other embodiments, CD4$^{LVFOXP3}$ T cells comprising a T cell receptor specific for an antigen of interest are used to dampen adaptive antigen-specific immune responses to the antigen of interest selectively. The antigen specificity of a Treg-like cell can be controlled by further genetic modification of a CD4$^+$ T lymphocyte to include an exogenous T cell receptor or chimeric antigen receptor (CAR) having a desired antigen specificity. For known antigens, including without limitation autoantigens, T cells can be isolated by MHC-peptide tetramers and then transduced and expanded.

Treg deficiency and autoimmune and other inflammatory conditions that may be treated with engineered CD4$^{LVFOXP3}$ T cells by the methods described herein include, but are not limited to, immune dysregulation polyendocrinopathy enteropathy X-linked (IPEX) syndrome.

Other conditions associated with autoimmunity and undesirable inflammation include, for example, multiple sclerosis (MS), rheumatoid arthritis (RA), reactive arthritis, psoriasis, pemphigus vulgaris, Sjogren's disease, autoimmune thyroid disease (AITD), Hashimoto's thyroiditis, myasthenia gravis, diabetes mellitus type 1, stomatitis, lupus erythematosus, acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic dermatitis, autoimmune aplastic anemia, autoimmune enteropathy, autoimmune hemolytic anemia, autoimmune hemolytic anemia, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaff's encephalitis, Blau syndrome, Bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, diffuse cutaneous systemic sclerosis, Dressler's syndrome, eczema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease (LAD), lupoid hepatitis, Majeed syndrome, Meniere's disease, microscopic polyangiitis, Miller-Fisher syndrome, mixed connective tissue disease, morphea, Mucha-Habermann disease, microscopic colitis, myositis, narcolepsy, neuromyelitis optica, neuromyotonia, occular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatic fever, sarcoidosis, Schmidt syndrome, Schnitzler syndrome, scleritis, scleroderma, serum sickness, Sjögren's syndrome, spondyloarthropathy, Still's disease, Stiff person syndrome, Subacute bacterial endocarditis (SBE), Susac's syndrome, Sweet's syndrome, Sydenham chorea, sympathetic ophthalmia, Takayasu's arteritis, temporal arteritis, thrombocytopenia, Tolosa-Hunt syndrome, transverse myelitis, undifferentiated connective tissue disease, undifferentiated spondyloarthropathy, urticarial vasculitis, vasculitis, vitiligo, Wegener's granulomatosis, autoimmune cardiomyopathy, ischemic heart disease, atherosclerosis, cancer, fibrosis, inflammatory bowel disease, inflammatory myopathy, giant cell arteritis (GCA), asthma, allergy, Parkinson's disease, schizophrenia, Alzheimer's disease, and acute respiratory distress syndrome ARDS, e.g. resulting from coronavirus infection.

Treatment of primates, more particularly humans is of interest, but other mammals may also benefit from treatment, particularly domestic animals such as equine, bovine, ovine, feline, canine, murine, lagomorpha, and the like.

Pharmaceutical Compositions

Pharmaceutical compositions can be prepared by formulating the CD4$^{LVFOXP3}$ T cells (i.e., CD4$^+$ T lymphocytes transduced with a lentiviral vector expressing FOXP3) into dosage forms by known pharmaceutical methods. For example, a pharmaceutical composition comprising CD4$^{LVFOXP3}$ T cells can be formulated for parenteral administration, as liquids, suspensions, emulsions, and injections (such as venous injections, drip injections, and the like).

In formulation into these dosage forms, the CD4$^{LVFOXP3}$ T cells can be combined as appropriate, with pharmaceutically acceptable carriers or media, in particular, sterile water and physiological saline, vegetable oils, resolvents, bases, emulsifiers, suspending agents, surfactants, stabilizers, vehicles, antiseptics, binders, diluents, tonicity agents, soothing agents, bulking agents, disintegrants, buffering agents, coating agents, lubricants, coloring agents, solution adjuvants, or other additives. The CD4$^{LVFOXP3}$ T cells cells may be also used in combination with known pharmaceutical compositions, immunosuppressants, cytokines, or other therapeutic agents.

In some embodiments, the pharmaceutical composition comprising the CD4$^{LVFOXP3}$ T cells is a sustained-release formulation, or a formulation that is administered using a sustained-release device. Such devices are well known in the art, and include, for example, transdermal patches, and miniature implantable pumps that can provide for delivery of the CD4$^{LVFOXP3}$ T cells over time in a continuous, steady-state fashion at a variety of doses to achieve a sustained-release effect with a non-sustained-release pharmaceutical composition.

Usually, but not always, the subject who receives the CD4$^{LVFOXP3}$ T cells (i.e., the recipient) is also the subject from whom the original, unmodified CD4$^+$ T lymphocytes (from which the CD4$^{LVFOXP3}$ T cells are produced) are harvested or obtained, which provides the advantage that the donated cells are autologous. However, CD4$^+$ T lymphocytes can be obtained from another unrelated subject (i.e., donor), a culture of cells from a donor, or from established cell culture lines. CD4$^+$ T lymphocytes may be obtained from the same species than the subject to be treated, and more preferably of the same immunological profile as the subject. Such cells can be obtained, for example, from a biological sample comprising CD4$^+$ T lymphocytes from a close relative or matched donor, and the CD4$^{LVFOXP3}$ T cells that are produced (i.e., by transduction with a lentiviral vector expressing FOXP3) can be administered to a subject in need of treatment for an inflammatory condition.

In certain embodiments, the CD4$^{LVFOXP3}$ T cells that are administered to a subject are derived from autologous or allogeneic CD4$^+$ T lymphocytes. The patients or subjects who donate or receive the cells are typically mammalian, and usually human. However, this need not always be the case, as veterinary applications are also contemplated.

Additionally, CD4$^{LVFOXP3}$ T cells may be expanded in culture prior to administration to a subject. In some embodiments, IL-2 is added to a culture to help stabilize and expand the number of CD4$^{LVFOXP3}$ T cells. In addition, a heparan sulfate-containing proteoglycan or heparin may be added to the culture to improve utilization of IL-2 by the CD4$^{LVFOXP3}$ T cells. For a description of techniques for culturing T cells, see, e.g., *Regulatory T Cells: Methods and Protocols* (Methods in Molecular Biology, Vol. 707, G. Kassiotis and A. Liston eds., Humana Press, 2011), Raulf-Heimsoth "T Cell—Primary Culture from Peripheral Blood" *Allergy Methods and Protocols* pp 17-30 (Humana Press Inc., Totowa, NJ, 2008); herein incorporated by reference in their entireties.

Administration

At least one therapeutically effective cycle of treatment with CD4$^{LVFOXP3}$ T cells (i.e., CD4$^+$ T lymphocytes transduced with a lentiviral vector expressing FOXP3) will be administered to a subject for treatment of an inflammatory condition. By "therapeutically effective dose or amount" of a composition comprising CD4$^{LVFOXP3}$ T cells is intended an amount that, when administered as described herein, brings about a positive therapeutic response, such as improved recovery from an inflammatory condition benefitting from increased immunological tolerance, such as an autoimmune disorder, an allergy, acute inflammatory syndromes, graft-versus-host disease, or a tissue transplant. The administration of cells has a clinically acceptable safety profile. Improved recovery may include a reduction in inflammation, pain, or autoimmune-induced tissue damage, decreased allergic response, or prolonged survival of transplanted tissue or organs. Additionally, a therapeutically effective dose or amount may compensate for Treg-deficiency (e.g., IPEX syndrome) and reduce the need for immunosuppressive or anti-inflammatory drugs.

In certain embodiments, multiple therapeutically effective doses of compositions comprising CD4$^{LVFOXP3}$ T cells and/or one or more other therapeutic agents, such as other drugs for treating immune diseases or conditions, or other medications will be administered. The compositions of the present invention are typically, although not necessarily, administered via injection (subcutaneously, intravenously, intraarterially, or intramuscularly), by infusion, or locally. Additional modes of administration are also contemplated, such as intraperitoneal, intrathecal, intralymphatic, intravascular, intralesion, transdermal, intraarticular, and so forth. In some embodiments, the CD4$^{LVFOXP3}$ T cells are administered locally, for example, to the site of a tissue or organ transplant or an inflamed region needing treatment. The pharmaceutical compositions comprising CD4$^{LVFOXP3}$ T cells and other agents may be administered using the same or different routes of administration in accordance with any medically acceptable method known in the art.

In another embodiment, the pharmaceutical compositions comprising CD4$^{LVFOXP3}$ T cells are administered prophylactically, e.g., to prevent Treg deficiency, etc. Such prophylactic uses will be of particular value for subjects who have a disease or a genetic predisposition to developing an inflammatory condition, such as an autoimmune disease, inflammation, or allergy. For example, CD4$^{LVFOXP3}$ T cells may be administered prior to transplant to prolong graft survival or to a patient with an autoimmune disease to prevent a disease flare, or in IPEX patients with mixed donor chimerism and disease relapse.

Those of ordinary skill in the art will appreciate which conditions compositions comprising CD4$^{LVFOXP3}$ T cells can effectively treat. The actual dose and number of doses to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Compositions comprising CD4$^{LVFOXP3}$ T cells, prepared as described herein (again, preferably provided as part of a pharmaceutical preparation), can be administered alone or in combination with one or more other therapeutic agents for treating an immune disease or condition, such as, but not limited to very low doses of immunosuppressive agents, such as steroidal agents (e.g., prednisone) or non-steroidal agents (e.g., mycophenolate, sirolimus (Rapamune, Wyeth-Ayerst Canada), tacrolimus (Prograf, Fujisawa Canada), 15-deoxyspergualin, cyclosporin, methotrexate, rapamycin, Rapamune (sirolimus/rapamycin), FK506, and Lisofylline (LSF); small molecules such as Jak-inhibitors; CTLA-4-Ig (Abatacept); and anti-inflammatory/analgesic agents, including, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; and immune selective anti-inflammatory derivatives (ImSAIDs); or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

Compositions comprising CD4$^{LVFOXP3}$ T cells can be administered prior to, concurrent with, or subsequent to other agents. If provided at the same time as other agents, the CD4$^{LVFOXP3}$ T cells can be provided in the same or in a different composition. Thus, the CD4$^{LVFOXP3}$ T cells and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising CD4$^{LVFOXP3}$ T cells and a dose of a pharmaceutical composition comprising at least one other agent, such as a drug for treating an immune disease or condition, which in combination comprise a therapeutically effective dose, according to a particular dosing regimen. Similarly, the CD4$^{LVFOXP3}$ T cells and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Kits

Any of the compositions described herein may be included in a kit. For example, CD4$^{LVFOXP3}$ T cells (i.e., CD4$^+$ T lymphocytes transduced with a lentiviral vector expressing FOXP3) may be included in a kit. Alternatively, a recombinant lentiviral vector, as described herein, for expression of FOXP3 in CD4$^+$ T lymphocytes to produce CD4$^{LVFOXP3}$ T cells may be included in the kit. In some embodiments, untransduced CD4$^+$ T lymphocytes are provided with the lentiviral vector separate. The kit may also comprise transfection agents, agents for purification of cells (e.g., microbeads for selection of transfected cells having the NGFR surface marker), agents for maintaining or culturing cells, such as media, and optionally one or more other factors, such as cytokines (e.g., IL-2), growth factors, antibiotics, and the like.

Such kits generally will comprise, in suitable means, distinct containers for each individual reagent or solution. The kit may comprise one or more containers holding the CD4$^{LVFOXP3}$ T cells and/or lentiviral vector, and other agents. Suitable containers for the compositions include, for example, bottles, vials, syringes, and test tubes. Containers can be formed from a variety of materials, including glass or plastic. A container may have a sterile access port (for example, the container may be a vial having a stopper pierceable by a hypodermic injection needle).

The kit can further comprise a container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for methods of treating inflammatory conditions with the CD4$^{LVFOXP3}$ T cells, as described herein. The package insert can be an unapproved draft package insert or can be a package insert approved by the Food and Drug Administration (FDA) or other regulatory body.

In one embodiment, the kit comprises a lentiviral expression vector comprising the components arranged as depicted in the vector map shown in FIG. 2. In another embodiment, the kit comprises a recombinant lentiviral vector comprising the nucleotide sequence of SEQ ID NO:2 or a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the recombinant lentiviral vector is capable of generating a Treg-like cell by transfection of a CD4$^+$ T lymphocyte.

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention.

Example 1

FOXP3 Engineered CD4$^+$ T Cells for Treg-Based Immunotherapy of IPEX Syndrome

FOXP3 is a transcription factor essential for the function of T regulatory (Treg) cells, a key CD4$^+$ T cell subset for control of immune responses and maintenance of immune tolerance. Mutations of FOXP3 cause severe early onset autoimmunity in mice and man, due to loss of functional Treg cells. Typical clinical manifestations include severe refractory enteropathy, Type 1 Diabetes (T1D), eczema, cytopenia, hepatitis, nephritis and thyroiditis. The disease, Immune dysregulation Polyendocrinopathy Enteropathy X-linked (IPEX) Syndrome, was clinically described in 1982 in a family with 19 males affected, and in 2000 the causative gene, FOXP3 was confirmed in 7 additional IPEX patients. The link between FOXP3 gene, its importance in the functioning of Treg cells and preventing autoimmune manifestations was first demonstrated in transgenic and knock-out murine models in early 2003 (Bacchetta ANN NYA Science, 2016). Bacchetta, R. et al. (2006) published the first data demonstrating that IPEX patients' Treg cells have impaired regulatory function (Bacchetta JCI, 2006).

The genetic reprogramming of mammalian cells for clinical purposes has recently become an available option, with the completion of clinical trials for the treatment of genetic diseases and their translation in market-authorized therapies. To control the devastating autoimmunity resulting from mutations of FOXP3 in IPEX syndrome, adoptive transfer of functional autologous Tregs generated in vitro by wildtype FOXP3 enforced expression using lentiviral-mediated gene transfer is performed.

Engineered murine FOXP3 over-expression as a method to generate Treg cells has been previously attempted in murine cells. In human cells, however, the expression pattern and function of FOXP3 are more complex, and retrovirus-mediated overexpression of FOXP3 does not consistently result in the generation of potent suppressive T cells in vitro, mainly due to unstable and activation dependent retroviral-mediated transgene expression (Allan S E., 2005). However, we found that lentivirus-mediated expression of FOXP3 under the control of the human elongation factor EF1α promoter can efficiently convert T effector into Treg cells (Allan S E, 2008).

Transduction of peripheral CD4$^+$ T lymphocytes with LVFOXP3 and in vitro expansion of transduced cells led to the generation of a homogeneous pool of T cells constitutively expressing FOXP3 at high intensity. The resulting CD4$^{LVFOXP3}$ behave as functional and stable FOXP3$^+$-CD4$^{LVFOXP3}$ T cells, with potent in vitro suppressive activity, reduced proliferative capacity, and decreased cytokine production (Allan et al., 2008; Passerini et al., 2013). CD4$^{LVFOXP3}$ stably express FOXP3 independent of activation, in steady-state, and inflammatory conditions, especially when generated from naïve T cells, and maintain inhibitory functions in vivo in a model of xenogeneic-GvHD (Passerini et al., 2013).

CD4$^{LVFOXP3}$ can be obtained from total CD4$^+$ T cells, rendering the manufacturing process easy and cost-effective because CD4$^+$ T cells are present at high frequency (about 40% of the lymphocytes) in the peripheral blood and there is an available standardized process to isolate CD4$^+$ T cells in high numbers from peripheral blood. CD4$^{LVFOXP3}$ require limited in vitro expansion with cytokines. The current preclinical small-scale method for the generation of CD4$^{LVFOXP3}$ resulted in up to 5 to 10-fold expansion in a 3-week-culture.

The preclinical studies described here assess the feasibility, safety and impact on disease manifestations of LVFOXP3 gene transfer in CD4$^+$ T cells to develop the CD4$^{LVFOXP3}$ as a biotherapeutic for administration in IPEX patients.

Example 2

FOXP3 Gene Transfer into Autologous CD4$^+$ T Cells

FOXP3+T regulatory (Treg) cells are a specific CD4$^+$ T cell subset for maintaining immune homeostasis and controlling undesired immune responses. We can convert CD4$^+$ T cells into Treg cells using LV-mediated FOXP3 gene transfer (Allan S E. et al, Mol Therapy 2008; Passerini L. et al, Sci Transl Med 2013). To obtain CD4$^{LVFOXP3}$ by FOXP3 gene transfer into autologous CD4$^+$ T cells to be used for clinical purposes, we have:

1) modified the vector to make it GMP-compliant, a third-generation bidirectional lentiviral vector containing the full-length cDNA of FOXP3, expressed under the EF1α promoter and NGFR, a marker gene, expressed under the minimal CMV promoter from the opposite strand, providing a cell surface marker for selection of transduced cells, and 2) developed a robust GMP-compliant method of gene transduction in CD4+ T cells followed by purification and expansion of the CD4$^{LVFOXP3}$.

The use of a strong EF1α promoter to drive wild-type FOXP3 expression ensures high transgene expression in the transduced cells. The resulting FOXP3 gene transferred CD4$^{LVFOXP3}$ acquire phenotypic and functional features of Treg cells. CD4$^{LVFOXP3}$ display high FOXP3 expression, and as a consequence they show high CD25 and low CD127, become low proliferative, produce low or no cytokines and, like naturally occurring Treg cells, have the ability to suppress the proliferation and cytokine production by T effector (Teff) cells in vitro. In addition, the use of a bidirectional vector gives simultaneous expression of the marker gene, truncated nerve growth factor receptor (NGFR), which enables purification of the modified T cells in vitro and their tracing in vivo. Similarly to Treg cells, CD4$^{LVFOXP3}$ T cells exert their suppressive activity in vivo in the xenogeneic graft-versus-host-disease (GvHD) mouse model. This is an established model to assess the ability of human Treg cells to control Teff cells responses by increasing mice survival and preventing weight loss.

In addition, we have demonstrated that the CD4$^{LVFOXP3}$ T cells also exert their suppressive activity in vivo in a hu-mouse model in which the FOXP3-deficient human stem cells engraft a mouse, and FOXP3-deficient T cells that reconstitute show CD4+ memory T cell proliferation, resembling what occurs in IPEX patients. CD4$^{LVFOXP3}$ T cells can prevent this lymphoproliferation and normalize survival in this model. The data show that CD4$^{LVFOXP3}$ T cells are not impeding an ongoing immune response to pathogens or tumor clearance, supporting the safety of this cell product.

The pre-clinical data demonstrates that LVFOXP3 provides efficient functional gene transduction in CD4+ obtained from both healthy individuals and IPEX patients with different FOXP3 mutations. In addition, we show functional equivalence using CD4$^{LVFOXP3}$ allogenic or autologous to the responder effector T cells.

We have applied the FOXP3 gene transfer technology to obtain Treg cells from CD4+ T cells from several IPEX patients with different FOXP3 gene mutations, each of which cause severe autoimmune manifestations and immune dysregulation. In IPEX syndrome there are no functional Treg cells and patients have autoimmunity from birth. The IPEX CD4$^{LVFOXP3}$ have identical cellular markers, anergic phenotype, cytokine production and suppressive function to naturally occurring Treg cells obtained from healthy donors, suggesting they could support restoration of immune regulation. CD4$^{LVFOXP3}$ T cells will be of great benefit in IPEX patients.

Example 3

CD4$^{LVFOXP3}$ Cell Product and Characteristics

CD4$^{LVFOXP3}$ T cells consists of autologous CD4+ T cells that have undergone lentiviral-mediated gene transfer of wild-type FOXP3 leading to persistent high FOXP3 expression and acquisition of regulatory T cell function.

Adoptive immunotherapy with CD4$^{LVFOXP3}$ T cells is proposed in subjects with IPEX syndrome to control the clinical manifestations of autoimmunity and immune dysregulation.

Autologous CD4$^{LVFOXP3}$ are infused in suspension by intravenous infusion, according to an escalating dose 3+3 Phase 1 clinical design (doses of $10^6$ cells/kg, $3\times10^6$ cells/kg or $10\times10^6$ cells/kg).

Example 4

Manufacturing Process

The manufacturing process for CD4$^{LVFOXP3}$ requires the isolation of patient CD4+ T cells from non-mobilized apheresis product followed by lentiviral-mediated gene transfer of wild-type FOXP3 and truncated nerve growth factor receptor (NGFR) with the recombinant lentiviral vector LVFOXP3. CD4$^{LVFOXP3}$ are manufactured, labeled, tracked and tested according to cGMP and Good Tissue Practice (GTPs) at the LCGM facility.

CD4+ T cells are isolated from non-mobilized apheresis by immunomagnetic separation using cGMP compliant reagents and devices (Miltenyi Prodigy system) on Day 0. Selected CD4+ T cells are cultured for up to 24 hours in X-VIVO 15 medium in the presence of 5% Human AB Serum, MACS® GMP T Cell TransAct™, IL-2 (100 U/mL) and IL-7 (10 ng/mL). On Day 1, cells are transduced with LVFOXP3. Transduced cells are cultured in X-VIVO 15 medium, or comparable medium suitable for large scale production, supplemented with 5% Human AB Serum, IL-2 (100 U/mL) and IL-15 (10 ng/mL) with periodic media addition and media exchange performed up to Day 8-10. At day 6-8 following activation, the transduced CD4+ T cells are selected for NGFR expression on the CliniMACS Plus instrument using CliniMACS CD271 reagent (NGFR microbeads). Post-enrichment, cells are cultured in X-VIVO 15 medium supplemented with 5% Human AB Serum, IL-2 (100 U/ml) and IL-15 (10 ng/mL). The transduced selected CD4+ cells are re-stimulated by the addition of MACS® GMP T Cell TransAct™ and cells are split for further expansion. CD4$^{LVFOXP3}$ are harvested between Days 16-21. Cells are washed and re-suspended in CryoStor CS-5 at a density of $5-100\times10^6$ cells/mL.

The CD4$^{LVFOXP3}$ manufacturing plan is summarized in FIG. 1 and the reagents used in this process are summarized in Table 1.

TABLE 1

| Critical Components and Reagents for CD4$^{LVFOXP3}$ Production | | | |
| --- | --- | --- | --- |
| Item | Manufacturer | Application | Standard |
| LVFOXP3 | Lentigen, Gaithersburg, MD | Transduction of patient CD4+ cells for FOXP3 gene transfer | As described below for transfer plasmid components, and per Lentigen Biologies Master File, reference to be included in IND submission |

TABLE 1-continued

Critical Components and Reagents for CD4$^{LVFOXP3}$ Production

| Item | Manufacturer | Application | Standard |
|------|-------------|-------------|----------|
| CliniMACS LS Tubing Set | Miltenyi Biotec, Bergisch-Gladbach, Germany | Immunomagnetic cell selection | Per DMF BB-MF 15499 |
| CliniMACS Prodigy TS 520 Tubing Set | Miltenyi Biotec, Bergisch-Gladbach, Germany | Immunomagnetic cell selection | Per DMF BB-MF 16214 |
| CliniMACS PBS-EDTA Buffer | Miltenyi Biotec, Bergisch-Gladbach, Germany | Immunomagnetic cell selection | Per DMF BB-MF-12541 |
| CliniMACS CD4 Reagent (Murine IgG$_1$) | Miltenyi Biotec, Bergisch-Gladbach, Germany | CD4$^+$ cell selection | Per DMF BB-MF-12541 |
| CliniMACS CD271 Reagent | Miltenyi Biotec, Bergisch-Gladbach, Germany | NGFR$^+$ cell selection | Per DMF BB-MF 15499 |
| Albumin (Human) USP, Albutein ® 25% | Nova Biologies, Oceanside, CA | Buffer supplement | USP; manufactured from human plasma units collected in USA plasmapheresis centers licensed by the FDA |
| X-Vivo 15 Medium | Lonza, Basel, Switzerland | CD4$^+$ cell culture | Manufactured according to GMP standards |
| MACS ® GMP TCell TransAct ™ | Miltenyi Biotec Bergisch-Gladbach, Germany | CD4$^+$ cell culture | Per DMF BB-MF 17483 |
| IL-2 | Prometheus Laboratories, Inc. San Diego, CA | CD4$^+$ cell culture | Manufactured according to GMP standards |
| CellGenix ® rh IL-7, or equivalent | CellGenix, Freiburg, Germany | CD4$^+$ cell culture | Manufactured according to GMP standards |
| CellGenix ® rh IL-15 | CellGenix, Freiburg, Germany | CD4$^+$ cell culture | Manufactured according to GMP standards |
| CryoStor ® CS5 | Biolife Solutions, Bothell, WA | Cryopreservative | Per DMF BB-MF-13671 |

Production and Purification of LVFOXP3

LVFOXP3, also referred to in previous publications as pCCL.FP3, is a recombinant bi-directional lentiviral vector in which expression of the Human Forkhead Box Protein 3 (FOXP3) therapeutic transgene is under the control of the human elongation factor 1a (EF1α) promoter, and NGFR gene encoding a truncated nerve growth factor receptor expressed under control of a minimal CMV promoter is included as a cell-surface marker for in vitro selection and in vivo tracking of transduced cells. The truncated NGFR was chosen as a marker gene because it is known to be safe and non-immunogenic in humans. A schematic of the vector genome illustrating the bi-directional nature of the respective expression cassettes is shown in FIG. 2A and a summary table of the transfer plasmid, pLVFOXP3, components are provided in FIG. 2B.

Apheresis is performed using either the Spectra Optia or COBE Spectra devices (Terumo BCT, Lakewood, CO) and follows current practices for autologous non-mobilized donor collections according to Standard Operating Procedures for apheresis at Lucille Packard Children's Hospital (LPCH) as described in the clinical protocol. The apheresis product is labeled and transported to the LCGM for manufacturing in a temperature monitored qualified carrier according to SOP-2008 Transport of Products To_From SHC-LPCH and within LCGM.

CD4$^+$ T cells are isolated from fresh apheresis products collected as described above. All washing, labeling and selection procedures are performed on the CliniMACS Prodigy System according to manufacturer's directions. Total nucleated cell count in the apheresis product is calculated using the Sysmex Analyzer (Beckman Coulter Inc, West Sacramento, CA). An aliquot is sent to the Quality Control unit of the LCGM for determination of the viable CD3$^+$ and CD4$^+$ cells using the LSR Fortessa X-20 or FACSCelesta flow-cytometry device (BD Biosciences, San Jose, CA). The Prodigy calculates the amount of human CD4 beads required for the selection based on the total number of CD4$^+$ cells. The cells are labeled—with anti-human CD4 microbeads as per the manufacturer's protocol. CliniMACS PBS-EDTA buffer supplemented with 0.5% HSA is used for the dilution, wash, incubation and elution steps. Post-selection, a sample of the CD4-enriched T cells are taken for determination of cell purity, yield, viability and recovery as assessed by flow-cytometry-based immunophenotypic analysis.

Following immunomagnetic CD4$^+$ cell selection, cells are cultured in medium for activation and polyclonal stimulation (Day 0-1). Specifically, CD4$^+$ cells are cultured in X-VIVO 15 medium supplemented with 5% HSA, MACS® GMP T Cell TransAct™, IL-2 (100 U/mL) and IL-7 (10 ng/mL) for up to 24 hours at a cell density of 1-2 E6 cells/mL.

After overnight stimulation, cells are transduced with LVFOXP3. The current transduction uses an MOI of 20. However, during process development, a titration is performed with GMP-process comparable vector to determine the optimal MOI for transduction. Following transduction, cells are cultured at 1-2E6 cells/mL in conditions as described above to promote cell expansion with demi-depletion performed every 1-2 days up to Day 7-9.

Following expansion, NGFR expressing CD4$^+$ T cells are enriched from the culture; all washing, labeling and selection procedures are performed on the CliniMACS Plus Instrument according to manufacturer's directions. Total nucleated cell count and viability in the culture is calculated using an automated cell counter. An aliquot is sent to the Quality Control unit of the LCGM for determination of the NGFR$^+$ cells using the LSR Fortessa X-20 flow-cytometry device (BD Biosciences, San Jose, CA). The total amount of human NGFR beads required for the selection is determined based on cell number and NGFR frequency. The cells are labeled with NGFR microbeads as per the manufacturer's protocol. CliniMACS PBS-EDTA buffer supplemented with 0.5% HSA is used for the dilution, wash, incubation and elution steps. Post-selection, a sample of the NGFR enriched T cells is taken for determination of cell purity, yield, viability and recovery as assessed by flow-cytometry-based immunophenotypic analysis.

Post-enrichment, NGFR expressing T cells are cultured in X-VIVO 15 medium supplemented with 5% HSA, IL-2 (100 U/ml) and IL-15 (10 ng/mL). The transduced CD4 cells are re-stimulated by the addition of MACS® GMP T Cell TransAct™. Cells are maintained at a cell concentration of 1-2E6 cells/mL with demi-depletion for medium exchange every 2-3 days.

After 16-21 days in culture, the CD4$^{LVFOXP3}$ are harvested, pelleted by centrifugation and re-suspended in cryo-protectant medium CryoStor CS5 at a concentration of 5-100×10$^6$ cells/mL in cryo-bags (Saint Gobain, Gathersberg, MD), frozen in a controlled rate freezer (Thermo Scientific) and stored in vapor phase liquid nitrogen.

Example 5

Specifications

Fresh or frozen formulated CD4$^{LVFOXP3}$ are considered final drug product and samples are tested as outlined in FIG. 1. CD4$^{LVFOXP3}$ that meets the product release criteria is released for infusion. Testing is designed to establish the purity, identity and safety of each batch of drug product. Based on previous data, the drug substance is expected to be comprised of ≥75% CD4$^+$ T cells of which ≥70% are FOXP3$^+$ at ≥70% viability. Given that stable and high FOXP3 expression of the transduced cells provides the phenotypic characteristics and functional properties of CD4$^{LVFOXP3}$ we will determine the FOXP3 and NGFR expression to confirm the cell product identity. The impact of the percentage of FOXP3 and NGFR double positive cells on in vitro suppression is determined to evaluate the potency release criteria for future Phase 2/3 studies.

The viral genome copy number of the CD4$^{LVFOXP3}$ drug substance is determined using a WPRE-based qPCR assay developed at the LCGM. This assay detects in the range of 0.003 to 33 viral genome copies per cell. The results from this assay is recorded for information only (FIO) during the Phase 1 study, and is used to inform a viral genome copy number per cell release criterion for Phase 2/3 studies.

Replication competent lentivirus (RCL) testing is performed on cells from production of CD4$^{LVFOXP3}$ using a Stanford LCGM-developed VSV-G-based qPCR assay for release of the drug product. The limit of detection in this assay is 10 copies of VSV-G in 100 ng genomic DNA, which has a detection rate of 97.92%. The false positive rate for this assay is 1.42%. Genomic DNA from the drug substance is tested in triplicate, and samples that are undetectable for VSV-G in 2/3 replicates are released for subject use. A sample of the drug product will also be sent to Indiana University Vector Production Facility for a full cell-based RCL assay. The final drug product will undergo safety testing based on established methods to confirm that the drug product has no detectable bacterial or fungal contamination.

Testing and Release Specifications for CD4$^{LVFOXP3}$

| Release Testing | Method | Assay Type | Proposed Specifications | Sample for Testing |
|---|---|---|---|---|
| Identity | Flow Cytometry | CD4$^+$ FOXP3$^+$ | ≥70% | Drug Substance |
| Purity | Flow Cytometry | CD4$^+$ | ≥75% | Drug Substance |
| Viability | Automated cell counter | Propidium Iodide and Acridine Orange | ≥70% viable cells | Drug Substance and Drug Product |
| Safety | Mycoplasma | PCR | undetected | Drug Product |
| Safety | Endotoxin | Limulus Amoebocyte Assay | <5 EU/kg body weight per hour | Drug Product |
| Safety | Sterility | Gram Stain | Undetected | Drug Product |
| Safety | Sterility | BacTec | No Growth for bacterial and fungal | Drug Product |
| Safety | Replication Competent Lentivirus | qPCR Cell Based | Undetectable Undetectable (Annual Reporting) | Drug Product Drug Product |

| Product Characterization | Method | Assay Type | Proposed Specifications | Sample for Testing |
|---|---|---|---|---|
| Safety | Vector Copy Number | WPRE based qPCR assay | For Information Only (FIO) | Drug Substance |
| Identity | Flow Cytometry | CD4$^+$ FOXP3$^+$ NGFR$^+$ | For Information Only (FIO) | Drug Substance |
| Potency | In vitro Suppression Assay | Flow cytometry | For Information Only (FIO) | Drug Substance |

Analytical Procedures

The Sysmex Analyzer (Beckman Coulter Inc, West Sacramento, CA) is used to determine the total nucleated cell count of the apheresis product. Cell viability of the apheresis product is determined by flow cytometry. The total nucleated cell count and viability of all other samples after the CD4$^+$ selection is determined using an automated cell counter according to manufacturer's directions.

Identity and purity determinations for phenotypic markers such as CD4, NGFR and FOXP3 is performed according to standard multiparameter flow cytometry procedures using monoclonal antibodies. Briefly, cells are re-suspended in PBS and then stained with a pre-determined amount of monoclonal antibody following manufacturer recommendation or based on titration results. Viability stain is included to ensure cell population identifications are based on viable cells only. Appropriate Control Sample is generated to ensure instrument, reagent and QC analyst proficiency per testing. For the need of detecting FOXP3, intracellular staining procedure is established to reach clear FOXP3$^+$ population separation. If needed, isotype control may be used to determine intracellular staining background. Stained samples are acquired by a BD Fortessa or BD Celesta Analytical Cytometer, and analyzed by BD FACSDiva software.

The suppressive capacity of CD4$^{LVFOXP3}$ is determined with an in vitro suppression assay (non-GMP). This assay is used to analyze the impact of the percentage of FOXP3$^+$ and NGFR$^+$ cells on suppression by CD4$^{LVFOXP3}$ in order to evaluate release criteria for future Phase 2/3 studies. In this assay, Responder CD4$^+$ T cells are labeled with a fluorescent dye, CellTrace™ CFSE, to measure cell proliferation. CD4$^{LVFOXP3}$ are labeled by a second fluorescent dye, CellTrace violet, which also measures cell proliferation. Responder CD4$^+$ T cells and CD4$^{LVFOXP3}$ are co-cultured at different concentrations after activation by Dynebeads Human T-cell Activator CD3/CD28. 96 hours after stimulation, proliferation of responder CD4$^+$ T cells is evaluated by flow cytometry. The suppression index is calculated as (% proliferation of responder–% proliferation of responder+ suppressor)/% proliferation of responder*100.

The absence of replication competent lentivirus (RCL) in the drug substance is confirmed using two assays: (1) a cell-based assay and (2) a qPCR-based assay that detects VSV-G. The cell-based RCL assay is performed at the Indiana University Vector Production Facility according to standard procedures. The results of the cell-based assay is reported in the IND annual report. The qPCR assay is performed at the LCGM according to standard procedures, and results of this assay is available at the time of product release.

In the RCL qPCR assay, a standard curve is generated using VSV-G plasmid DNA spiked into control human DNA. The total amount of VSV-G in the final product is interpolated from the standard curve. VSV-G is used as the positive control for RCL because although VSV-G protein is required for transduction of the target cells, VSV-G is co-transfected into the viral packaging cell line as a separate plasmid from that carrying the packaging signals and transgene of the provirus. Therefore, VSV-G DNA would only be present in the target cells in the event that a replication competent infectious lentivirus was formed. Positive control samples to determine the limit of detection are generated by creating a secondary dilution curve down to 50 copies per reaction. The 50 copies/reaction dilution is then added to control human DNA at 10, 8, 6, 5, 4, 3, 2, or 1 copies/ reaction.

The viral genome copy number is determined with a qPCR-based assay that detects the total copies of Woodchuck hepatitis virus posttranscriptional regulatory element (WPRE) per cell. WPRE was chosen for this assay as it is not present in untransduced human cells and is frequently used as a post-transcriptional regulatory element for many viral vectors. In this assay, a standard curve is generated using a WPRE-containing plasmid DNA spiked into control human DNA. The total copies of WPRE per cell is interpolated from this standard curve. Positive control samples for this assay are comprised of serial dilutions of genomic DNA from an H9-1C cell line. This cell line has a known single integration of WPRE. Human DNA from non-transduced cells is used as a negative control. Testing for lentiviral genome copies per cell is for information only and does not have a specification for Phase 1 studies, but clinical manufacturing experience is used to define a release criterion for Phase 2/3 studies.

Bacterial and fungal sterility testing of the cellular products are performed on the end of culture cell supernatant to preserve product for patient infusion by automatic Sterility device, BacTec. Inoculation of cultures Aerobic/F, Anaerobic/F, and Myco/F bottles is performed in the BSC in QC Laboratory in order to minimize handling of the samples outside of the cleanroom environment. All cultures are maintained for 14 (bacterial) or 42 days (fungal) by the Stanford Healthcare Clinical Microbiology Laboratory with final reports of "no growth detected" documented in the COA of all products in compliance with 21 CFR 610.12.

As the drug product may be administered to the patient prior to receiving full sterility results, two additional procedures are performed to ensure the safety of the drug product. First, a gram stain is done at the Stanford Healthcare Clinical Microbiology Laboratory according to standard operating procedures. The gram stain is a rapid method for assessing sterility that involves staining the drug product with crystal violet and safranin to detect Gram positive and Gram negative organisms, respectively. Second, an interim sterility sample is taken three days prior to harvest of the final drug product. This sample is tested by BacTec Inoculation of culture bottles as described above. In the unlikely event that a positive sterility test result is obtained after a cell product has been administered to the subject, an action plan is executed to notify the Principal Investigator. The details of this action plan and justification for administration prior to sterility results are available is included in the IND for this drug product.

Endotoxin testing is performed on the final formulated product. 0.5 ml aliquots of formulated product is assessed using the ENDOSAFE-PTS Chromogenic Assay (Charles River Laboratories, Wilmington, MA). The assay is performed at the facility performing the processing (LCGM). The assay is based on the Limulus Amoebocyte Assay. If bacterial endotoxin is present, a protease cascade is initiated, resulting in the release of a chromogenic substrate that can be detected and measured spectrophotometrically. The infusion rate of the final drug product is adjusted to not exceed 5 EU/kg body weight/hour required for all products in compliance with 21CFR§ 610.12 and USP <85>.

*Mycoplasma* testing is performed on end of culture supernatant and cells from production of CD4$^{LVFOXP3}$ using the Roche MycoTOOL Real-Time PCR Kit. The MycoTOOL PCR assay is FDA cleared, detects >140 species of *mycoplasma* and provides results in <5 hours from sample isolation using only 1 ml of culture supernatant. The limit of detection in this assay is 10 CFU/ml. Prior to licensing, a comparability study is conducted to demonstrate the rapid

*mycoplasma* detection method is as effective as the 28 day *mycoplasma* test USP *Mycoplasma* test and as specified under 21 CFR 610.30.

Cell number is based on the target dose for the dose cohort requirements. Safety testing specifications are set to show that the product is free of bacterial, fungal, *mycoplasma* and endotoxin contamination. Specifications for process intermediates and cell substances are based on the results of analysis of materials from at least 3 large scale process engineering runs performed according to the standard operating procedure anticipated to be used in the production of clinical materials. Since healthy donor apheresis is used for all engineering runs, specifications may be refined as additional data is collected during the clinical trial.

Appropriate standards and controls are used (where available) to verify the performance of raw materials, reagents, devices and assays used in the production, purification and testing of materials for clinical use.

Cells are cryopreserved in USP Class VI fluorinated ethylene propylene (FEP) KryoSure containers that are FDA 510(k) cleared (Saint Gobain, Gaithersburg, MD).

Stability studies are performed on drug products from qualification runs and will cover the maximum period expected for holding cells (up to 12 months). All drug products are tested for viability and identity. The drug product must retain ≥70% viability upon thaw and meet specifications for CD4$^+$ FOXP3$^+$ to be considered stable and infused into the patient.

These products are administered within 12 months of cryopreservation. We will record viability and identity at the time of thawing, but we do not anticipate storage of these products beyond this time. We therefore will not perform any long-term stability studies.

Example 6

In Vitro Pharmacology

The human FOXP3 coding sequence was cloned under the control of a constitutive promoter in a bi-directional *lenti*-viral-vector (LV) construct. This vector construct allows simultaneous expression of two transgenes under two independent promoters. In CD4$^{LVFOXP3}$, the two transgenes are encoding for the functionally specific full-length FOXP3 and for the cell-surface marker NGFR used to select and track the transduced T cells as originally described in Allan S et al. in which the vector was named pCCL.FP3. pCCL.FP3 is referred to as LVFOXP3 throughout this document. Naïve CD4$^+$ T cells were initially transduced with LVFOXP3 upon TCR-mediated preactivation with anti-CD3/CD28 mAbs or anti-CD3 mAb and antigen presenting cells (APC) in the presence of IL-2 and IL-7. Since FOXP3 expressing cells have reduced proliferative capacity, the transduced cells have to be purified in order to be tested and further expanded. Transduced cells purification can be easily performed by positive selection of NGFR$^+$ cells. Efficiency of transduction was high (86 sd 12%) with the control vector and lower (47 sd 18%) with LVFOXP3 because of the less efficient packaging of the larger viral genome. However, NGFR$^+$ cells purification consistently resulted in a homogeneous cell population to be assessed phenotypically and functionally. Unlike CD4$^+$ cells transduced with the "empty" control vector, LVFOXP3 CD4$^+$ transduced cells (CD4$^{LVFOXP3}$) homogeneously expressed FOXP3 and CD25 at comparable levels as expanded CD25hi Treg cells, and both cell types had low expression of CD127, as expected. The expression of FOXP3 in lentiviral LVFOXP3 transduced cells was persistent overtime after activation, which was superior to what was previously obtained when retroviral FOXP3 transduction was used. The percentage of FOXP3 positive cells in the CD4$^{LVFOXP3}$ prepared with LVFOXP3 remained high and stable for up to 4 weeks of culture.

CD4$^{LVFOXP3}$ showed the ability to suppress proliferation and IFN-γ production of activated CD4$^+$ responder T cells. The presence of CD4$^{LVFOXP3}$ cells in the co-culture inhibited the effector function of the responder cells in a cell dose dependent fashion and at comparable levels to ex-vivo isolated Treg (CD25hi T cells), whereas cells transduced with the control vector without FOXP3 (pCCL) did not acquire suppressive function. The suppressive activity of the CD4$^{LVFOXP3}$ cells was comparable when the transduction was established starting from naïve or memory CD4$^+$ T cells.

Overall these initial studies demonstrated the powerful and stable effect of the FOXP3 transduction in converting a CD4$^+$ T cell from an effector cell to a suppressor cell. The lentivirus-mediated FOXP3 transduced cells resembled naturally occurring CD25hi Treg cells peripherally isolated and tested fresh or after expansion, in terms of FOXP3, CD25 and CD127 expression and suppressive function. In addition, the lentivirus-mediated FOXP3 transduced cells expressed FOXP3 more persistently overtime and at higher levels as compared to retrovirus-mediated FOXP3 transduced cells or expanded Treg cells.

Figures 3A, 3B, 3C:
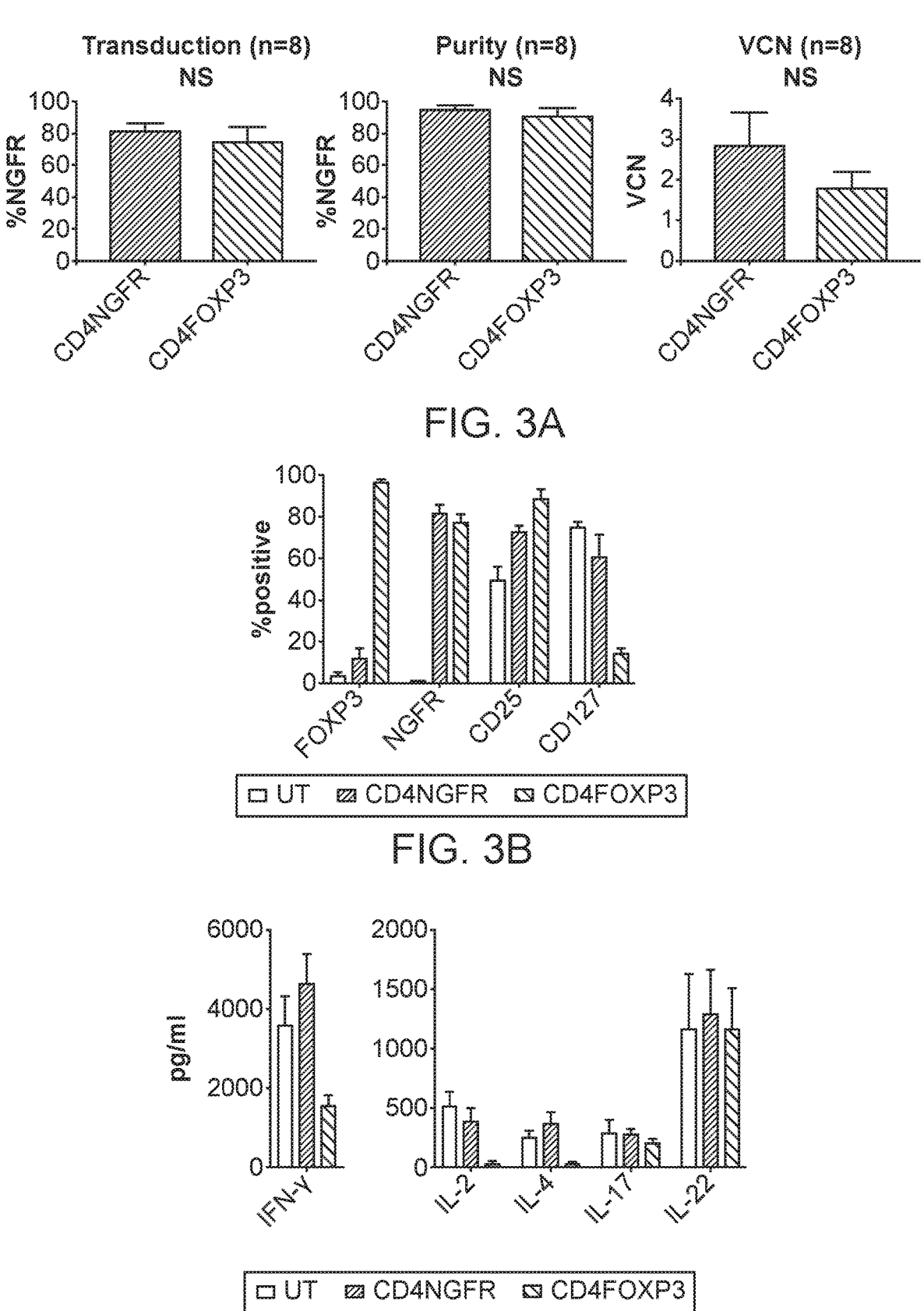
FIGS. 3A-3E show CD4$^{LVFOXP3}$ obtained upon optimization protocol from total CD4$^+$ T cells from healthy donors (n=8). (A) Transduction efficiency, measured as percentage of NGFR$^+$ cells, at day 6 post-transduction; purity of transduced cells measured at day 10 post-transduction as percentage of NGFR$^+$ cells and vector copy number measured by PCR at day 24 (end of culture). Results of CD4$^{LVFOXP3}$ (CD4FOXP3) and of CD4$^{LVNGFR}$ (CD4NGFR) control cells are shown. (B) Percentage of positive cells for FOXP3, NGFR, CD25 and CD127 at day 24. (C) Cytokine production by CD4$^{LVFOXP3}$ (CD4FOXP3) and of CD4$^{LVNGFR}$ (CD4NGFR) control cells. All cytokines are measured by ELISA. IL-2 at 24 hours and the other cytokines at 72 hours after anti-CD3/CD28 activation (1:25=bead: cell). (D) Expression of other Tregs-related molecules. CTLA4, PD-1, ICOS, HELIOS, GITR, IL-1R1, IL-6R, TIGIT, CD226, TIM3 and LAGS were measured by FACS. (n=6, MEAN+SEM) or (E) mRNA (FOXP3, NGFR, EOS, LGMN, IL-12A and EB13) were measured by real time PCR.
Figure 3D:
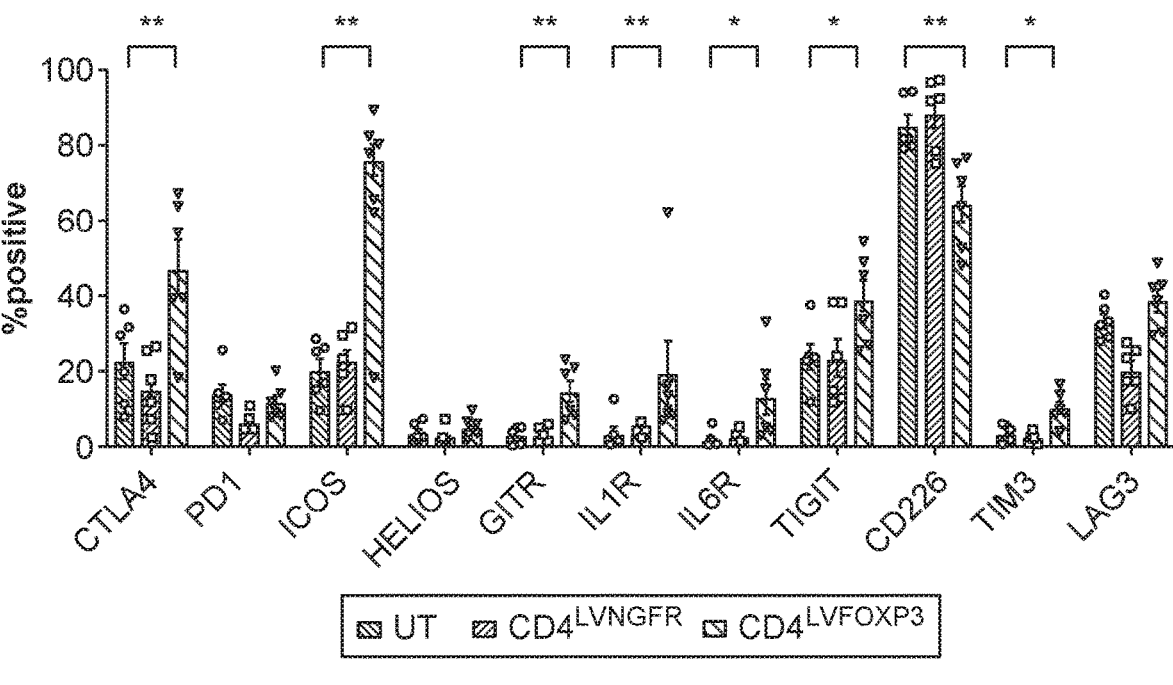
Figure 3E:
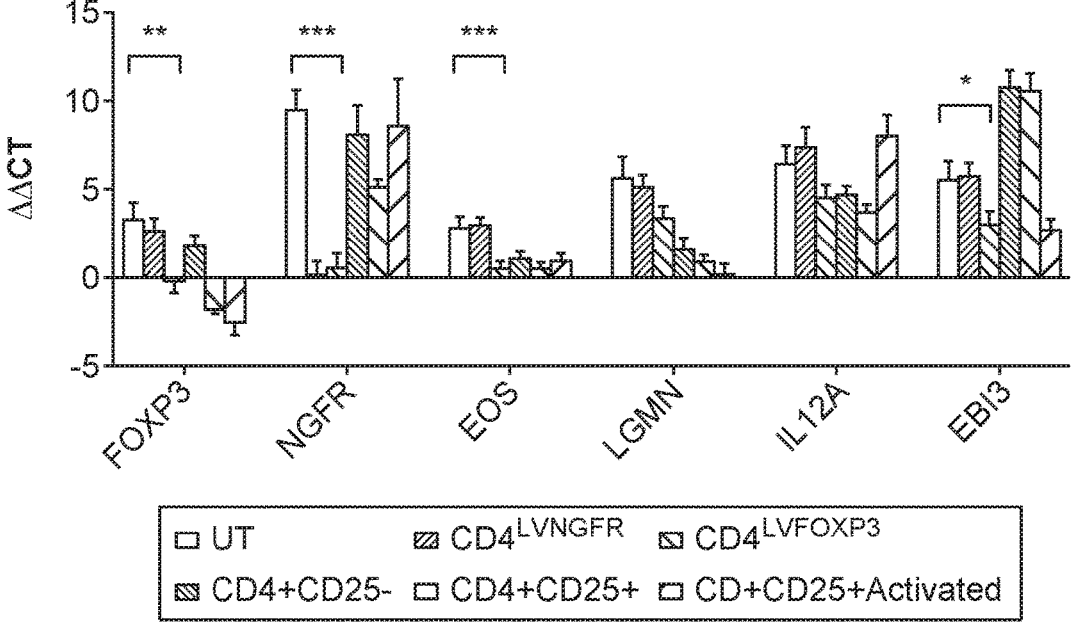

Recently, we performed validation and inter-laboratory reproducibility studies in additional healthy donors and IPEX patients. We first used the same LVFOXP3 construct and cell production method, and more recently, have been working towards establishing a more GMP compliant vector construct and cell production method. Briefly, we eliminated the presence of APC during the pre-transduction activation, and the presence of feeder cells during the reactivation for expansion. We have replaced both steps using TransAct, anti-CD3 and anti-CD28 coated nanoparticles (Miltenyi Biotec Inc,), that are commercially available GMP grade. In addition, we have discontinued the use of polybrene during transduction and have shortened the culture period by re-stimulating the purified NGFR$^+$ transduced cells at day 8-11 and expanding them for 8-10 days in order to shorten the total culture time from the original process. The reproducibility of the method with this optimization is demonstrated in FIG. 3 in terms of transduction efficiency, purity and vector copy number (FIG. 3*a*), FOXP3, NGFR, CD25 and CD127 expression (FIG. 3*b*) and cytokine production and coinhibitory membrane markers (FIG. 3*c-e*). The data reported are an example of a consistent production. Numbers may slightly change in the final Phase 1 product.

Figure 4A:
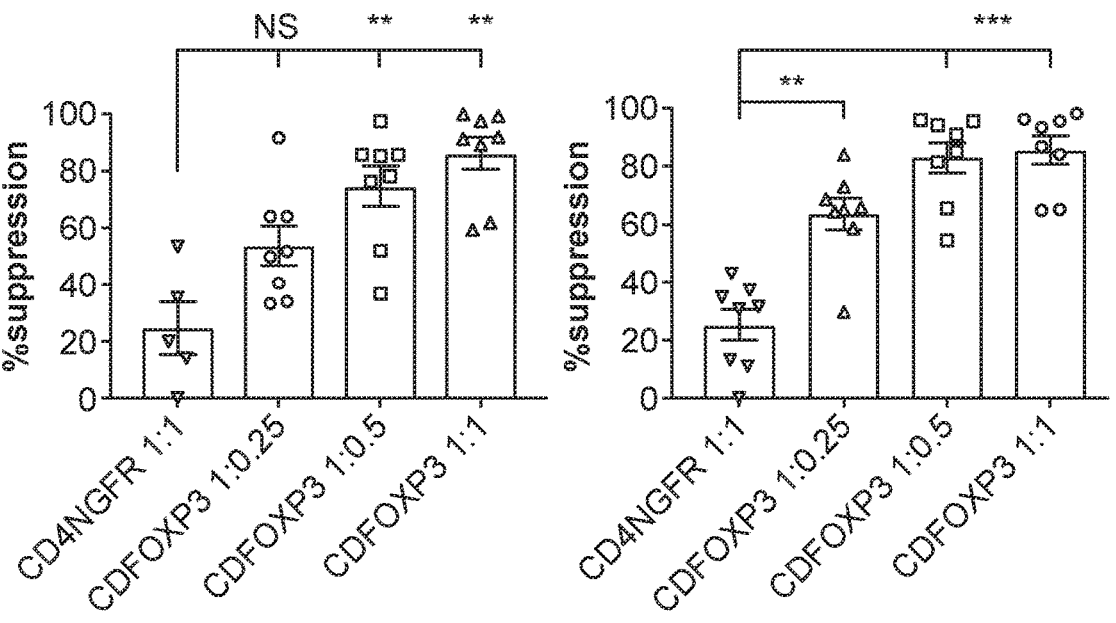
FIGS. 4A-4B show CD4$^{LVFOXP3}$ cells obtained upon optimization protocol from total CD4$^+$ T cells from healthy donors (n=8) and two IPEX patients. (A) Percentage of suppression (median and SEM) from 8 different donors obtained either with the previously described methods (APC/Feeder) or with the recently optimized method more GMP compliant (TransAct optimized cGMP). Proliferation of responder T cells was determined by CFSE staining and measured by division index after 4 days of activation. CD4$^{LVFOXP3}$ were added at different responder: suppressor cells ratios as indicated. (B) Percentage of suppression by CD4$^{LVFOXP3}$ obtained from IPEX #37, with c.1150 G>A and preserved endogenous mutFOXP3 and IPEX #64, c.1270_1272 delinsC which abrogates endogenous FOXP3 expression.
Figure 4B:
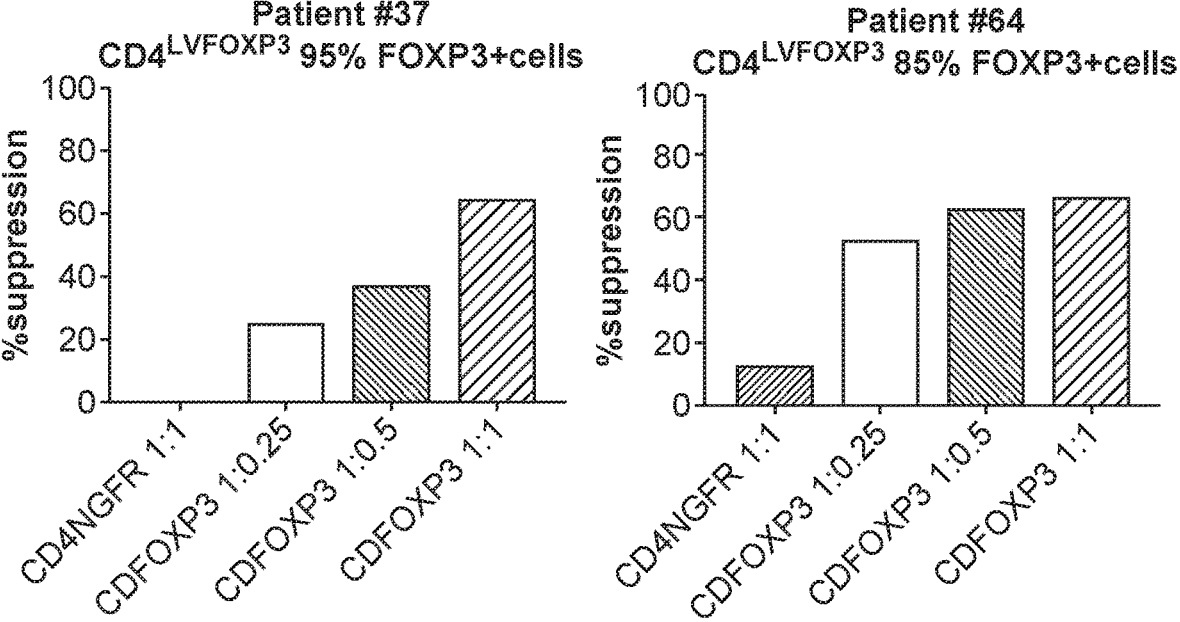

Consistent with previous results, the CD4$^{LVFOXP3}$ obtained at Stanford with the transferred method (alloAPC) or with the optimized cGMP method (TransAct), exert good suppressive activity when obtained from healthy donor samples (FIG. 4*a*). Functional CD4$^{LVFOXP3}$ were also obtained from two additional IPEX patients (FIG. 4*b*). Notably, IPEX Patient #37 is a young adult under chronic immunosuppression, whereas Patient #64 has severe acute IPEX with FOXP3 mutation that completely abrogated protein expression. The use of cells from these two patients shows that functional CD4$^{LVFOXP3}$ can be obtained even from T cells exposed to chronic immunosuppression, as well as from T cells completely lacking endogenous FOXP3.

Overall the results obtained comparing the two methods indicate the reproducibility and confirm that the use of the GMP compliant activation beads (TransACT™) allow production of conforming CD4$^{LVFOXP3}$. Expression of FOXP3 and NGFR was evaluated 10 days after culture on CD4$^{LVFOXP3}$, after re-stimulation and expansion. Suppressive activity of CD4$^{LVFOXP3}$ was measured at day 10 after re-stimulation, on a 4 days co-culture suppressive assay. We propose to use the data from small scale experiments as the measure of identity of the CD4$^{LVFOXP3}$ product (FOXP3$^+$ cells ≥70%) in the proposed trial. In addition, we propose to measure the percentage of NGFR$^+$ cells, which is not always as high as FOXP3, and suppression in vitro as an indication of potency of CD4$^{LVFOXP3}$ which may be further validated for use in future Phase 2 trials.

Figure 5:
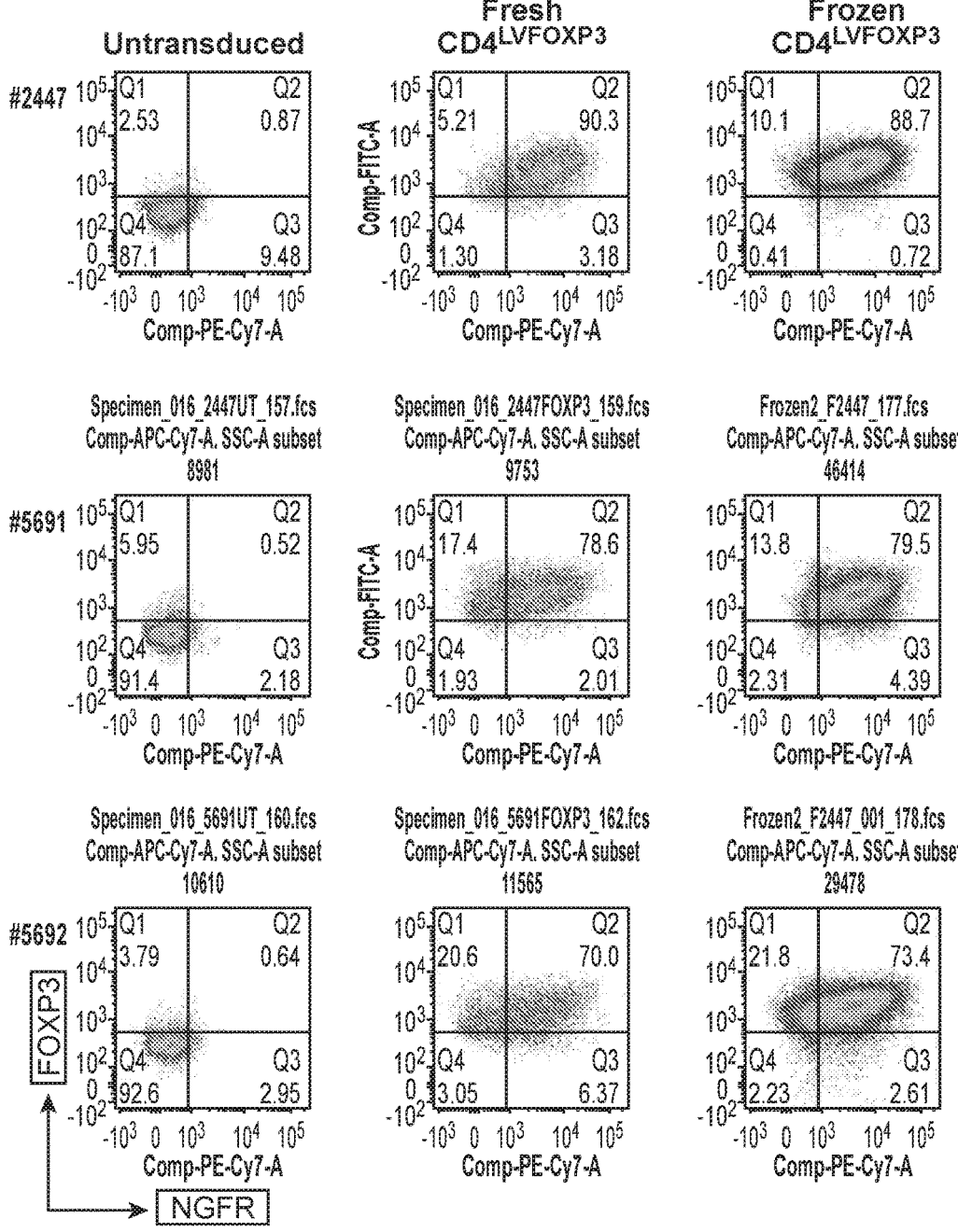
FIG. 5 shows an assessment of FOXP3 expression from fresh or frozen CD4$^{LVFOXP3}$. CD4$^{LVFOXP3}$ were either tested at the end of the culture (fresh) or were frozen and thawed (Frozen). The result of this experiment performed with cells from three different subjects is shown.

Moreover, the FOXP3 and NGFR phenotype is consistent when tested on fresh cells at the end of the culture or after freezing and thawing (FIG. 5).

Figures 6A, 6B:
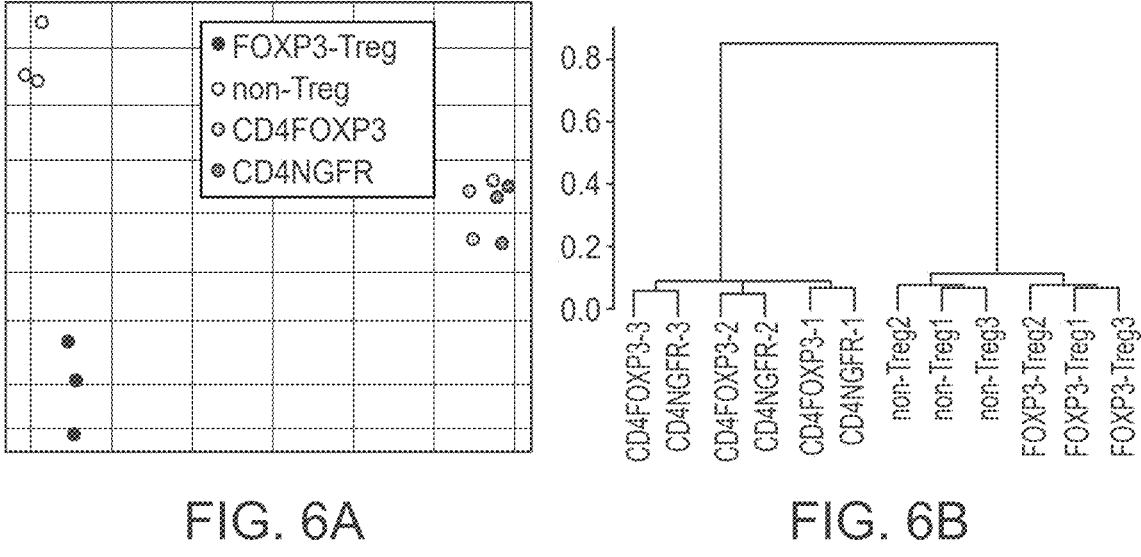
FIG. 6 shows the gene expression profile of the CD4$^{LVFOXP3}$ in comparison to freshly isolated Tregs or non-Tregs or controls transduced cells with NGFR only (no FOXP3). (a) Principle component analysis (PCA) (b) Hierarchical cluster analysis (HCA) (c) Shared DEGs (upregulated or downregulated) between FOXP3 Tregs and CD4$^{LVFOXP3}$ and the 7 genes shared between FOXP3 Tregs and CD4$^{LVFOXP3}$.
Figure 6C:
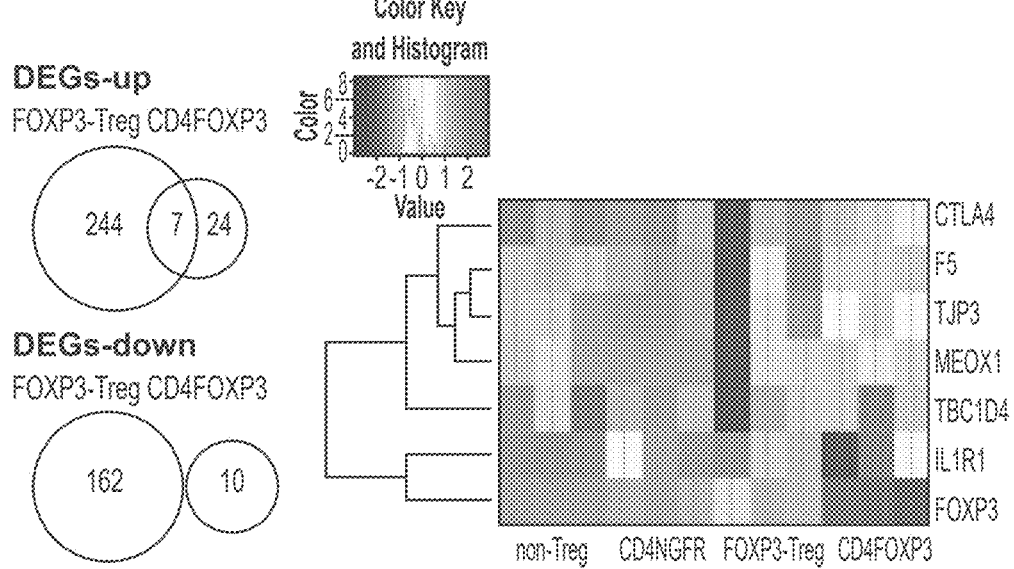
Figure 7:
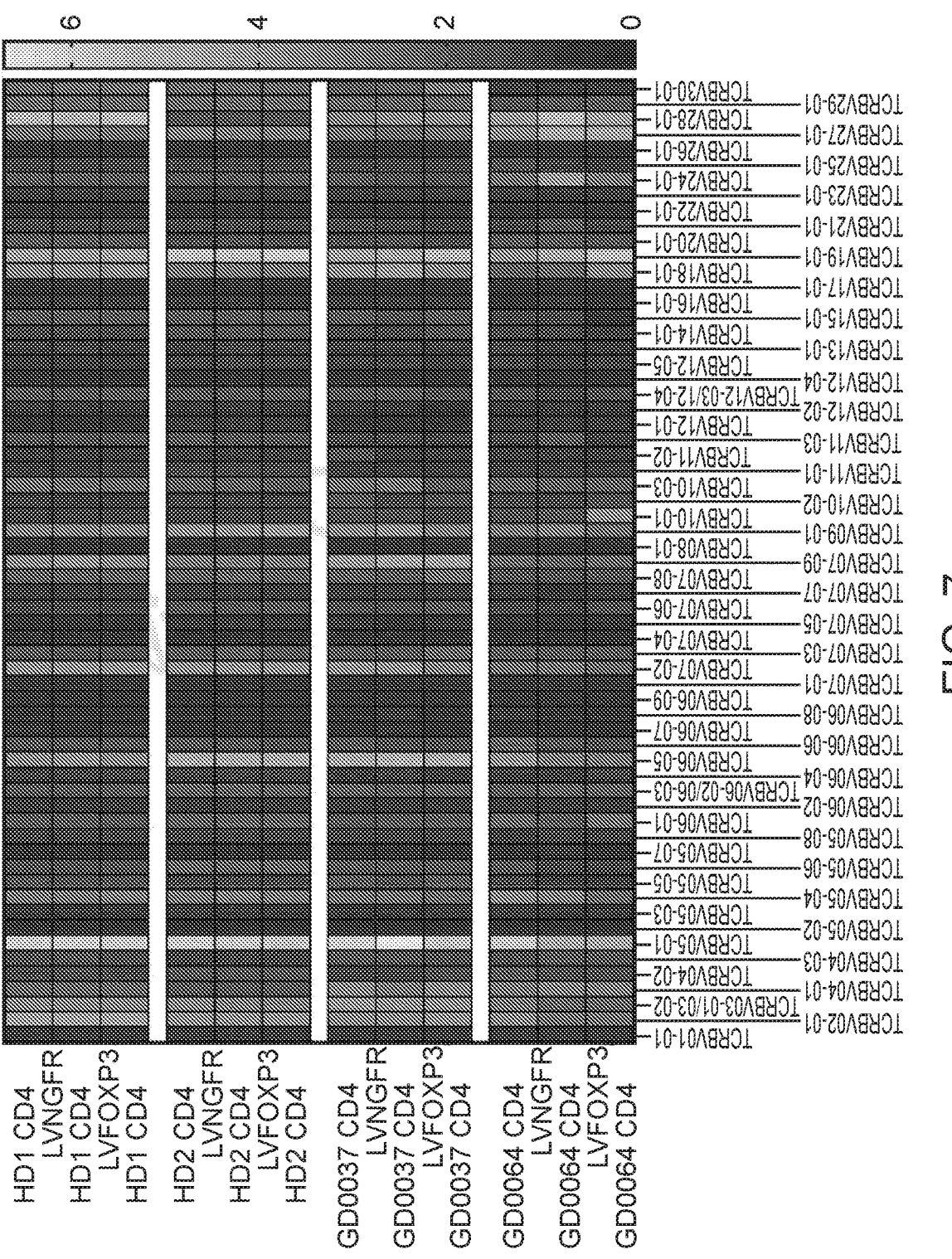
FIG. 7 shows that the TCR repertoire of CD4$^{LVFOXP3}$ remains polyclonal and similar to that of the starting population of CD4$^+$ T cells.

Lastly, the gene transcription profile of the CD4$^{LVFOXP3}$ T cells has been obtained from 3 healthy subjects and has been compared to that of Treg cells isolated from the same subjects. This comparison revealed that the CD4$^{LVFOXP3}$ T cells are overall divergent from Treg cells and more similar to expanded Teff cells but do overlap with Treg cells for a restricted core of 6 genes (plus of course FOXP3) (FIG. 6). These core 6 genes are differentially upregulated in Treg and in CD4$^{LVFOXP3}$ T cells, and they are most likely related to FOXP3 overexpression and the acquired suppressive function. In addition, the TCR repertoire of the CD4$^{LVFOXP3}$ T cells remains polyclonal and therefore similar to that of the original cells (FIG. 7).

Figures 8A, 8B, 8C, 8D:
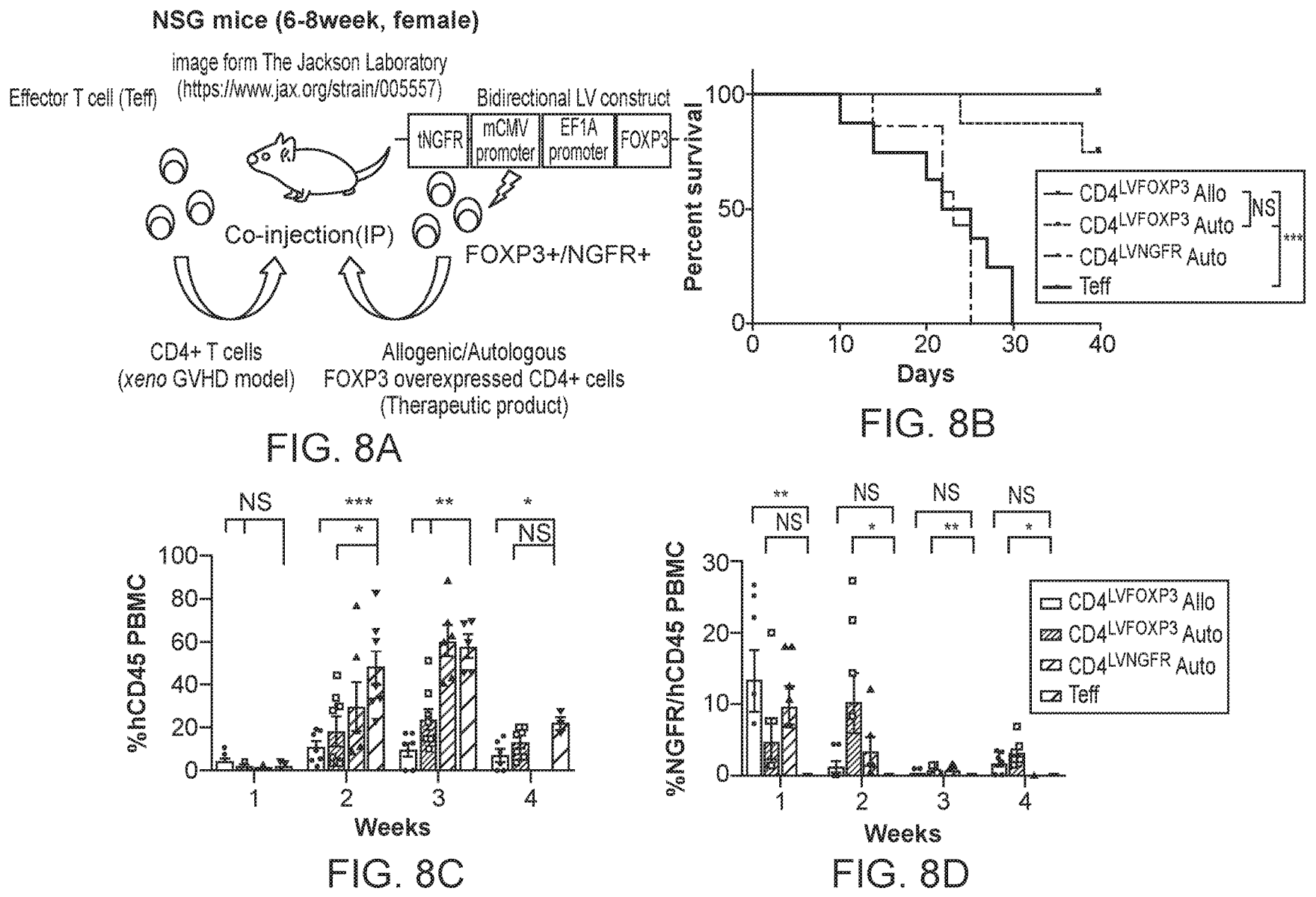

To test the efficacy of the CD4$^{LVFOXP3}$ in vivo, we utilized a widely accepted method for testing functional Treg cells, consisting of the ability of the Treg population to suppress the xenoGVHD reaction triggered by injection of human CD4$^+$ T cells in an immunodeficient mouse (NSG) sublethally irradiated (Hahn S A et al., 2015). Once injected, the human T cells engraft, expand and mount an immune response towards the mouse tissues, which cause weight loss, wasting and death of the mice within 2-3 weeks. In Passerini L. et al. we showed that cotransfer of human CD4$^+$ T cells (Teff) with CD4$^{LVFOXP3}$, but not with the control CD4$^{LVNGFR}$, promoted survival of 75% of the mice. CD4$^{LVFOXP3}$ prevented xenoGVHD reaction in 71% of the mice even when injected at day 6 after Teff cell administration (FIGS. 8a and b). Therefore CD4$^{LVFOXP3}$ showed the ability to prevent or control xenoGVHD reaction. In this hu-mouse model, CD4$^{LVFOXP3}$ were detected in the peripheral blood of the mice up to 14 days post injection, as NGFR$^+$ cells (FIG. 8c). These results indicate that these cells did not expand but rather declined as the Teff expanded in the control mice. In addition, when injected alone, CD4$^{LVFOXP3}$ did not caused xenoGVHD. The xenoGVHD model was also used to assess in vivo stability of the FOXP3 transduced T cells.

Figures 10A, 10B, 10C, 10D:
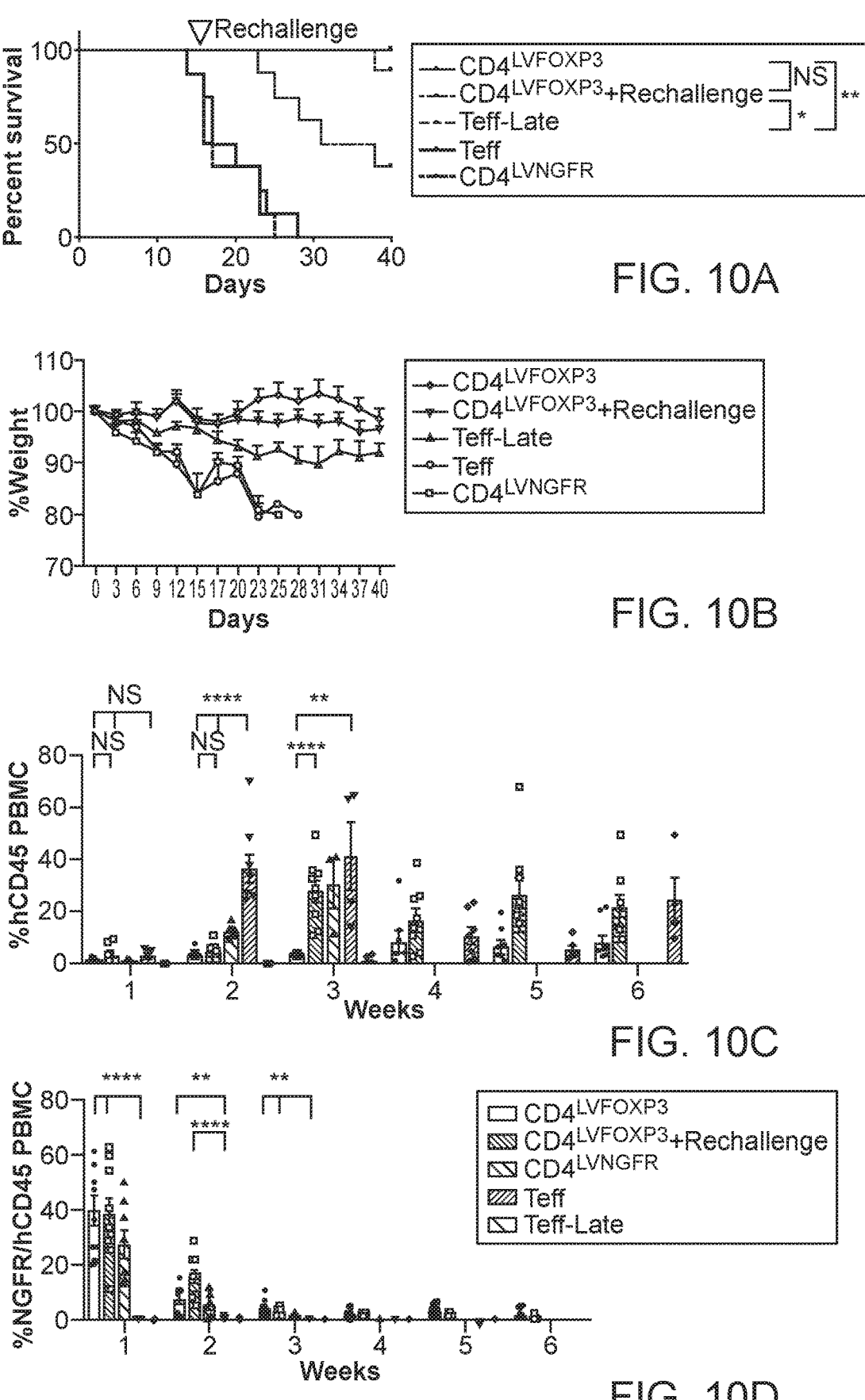
FIG. 10 shows rechallenge with CD4$^+$ Teff cells in a xenoGVHD hu-mouse model. Overall survival (a), weight (b), human CD45+ cell engraftment (c) and NGFR+ transduced cell engraftment (d) are shown. Sublethally irradiated mice were injected with human CD4$^+$ Teff cells alone (black line) or with CD4$^{LVFOXP3}$ (blue line) or control CD4$^{LVNGFR}$ (grey line). After one week the mice injected with Teff alone or with control CD4$^{LVNGFR}$ started to lose weight and by week 3 had to be sacrificed because of the xenoreaction, whereas the mice coinjected with CD4$^{LVFOXP3}$ continued to be healthy. At about week 2, these mice were re-injected with Teff cells at the same initial dose ($2\times10^6$/mouse). Despite re-challenge the mice that were previously exposed to CD4$^{LVFOXP3}$ did not develop xenoGVHD. As an additional control, some of the mice were injected with Teff alone for the first time (Teff-late, dashed line) in parallel to the rechallenged mice. Also, these mice died earlier than the CD4$^{LVFOXP3}$ and rechallenged mice.

Seven days after injection in the late transfer model, and therefore after being exposed to the inflammatory environment caused by irradiation and by expansion of the xeno-reactive Teff cells, CD4$^{LVFOXP3}$ were isolated from secondary lymphoid organs and analyzed for FOXP3, CTLA4 and CD25 expression (FIG. 10). All these markers were consistently higher in CD4$^{LVFOXP3}$ as compared to the control CD4$^{LVNGFR}$ that were FOXP3 negative and expressed low levels of CD25 and CTLA4. These data indicate the phenotypic stability of the CD4$^{LVFOXP3}$.

Figure 9:
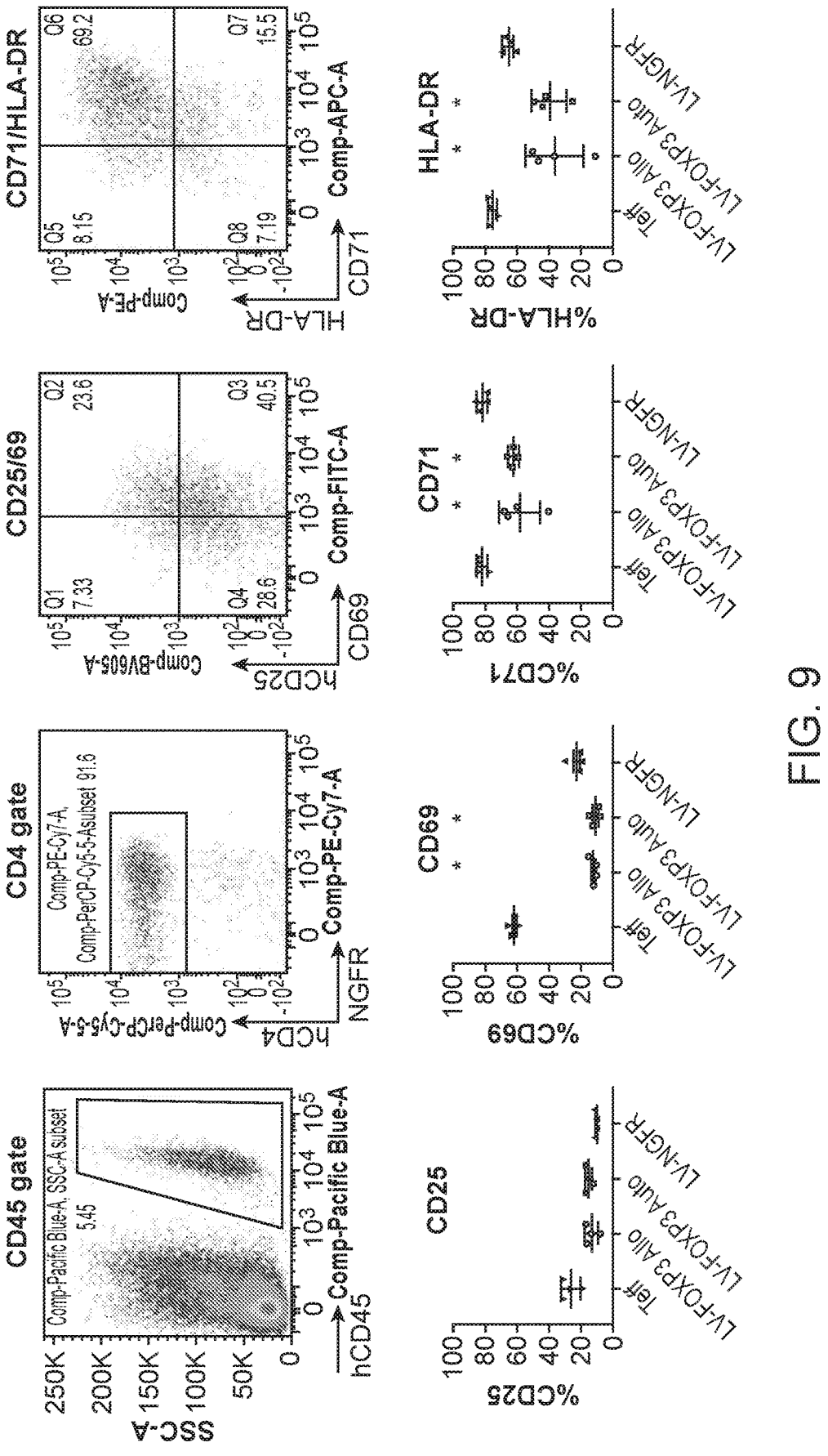
FIG. 9 shows the phenotype of human T cells obtained from the spleen of xenoGVHD-hu-mice treated or not with CD4$^{LVFOXP3}$. Results (dot plot) obtained from one mouse (above) and cumulative data from multiple mice (below) are shown, comparing mice injected with CD4$^+$ T cells alone (Teff) or co-injected with allogeneic or autologous CD4$^{LVFOXP3}$ (LVFOXP3 Allo and LVFOXP3 Auto, respectively) or control CD4$^{LVNGFR}$ (LVNGFR). CD45 expression indicates the human cell engraftment. CD25, CD69, CD71 and HLA-DR indicate activation markers. Despite comparable level of engraftment, T cells isolated from spleen of mice treated with CD4$^{LVFOXP3}$ expressed significantly lower levels of activation markers.

CD4$^{LVFOXP3}$ generated from IPEX patients were also tested in vivo and proved to be efficacious and comparable to healthy donor's CD4$^{LVFOXP3}$ in preventing xenoGVHD (FIG. 9). In all the experiments previously done in vivo, the responder Teff cells were allogeneic to the suppressor cells.

However, since we plan to inject autologous CD4$^{LVFOXP3}$ in IPEX patients, we tested in parallel autologous and allogeneic human xenoGVHD.

We demonstrated that both allogenic and autologous CD4$^{LVFOXP3}$ have the ability to prevent the xenoGVHD. Both had similar survival (14 days). In addition, at sacrifice, we collected the human T cells from the spleen of sacrificed (day 40) mice (NSG) and we showed a significant decrease in activation markers as compared to those expressed by cells obtained from the control mice.

Figures 11A, 11B, 11C:
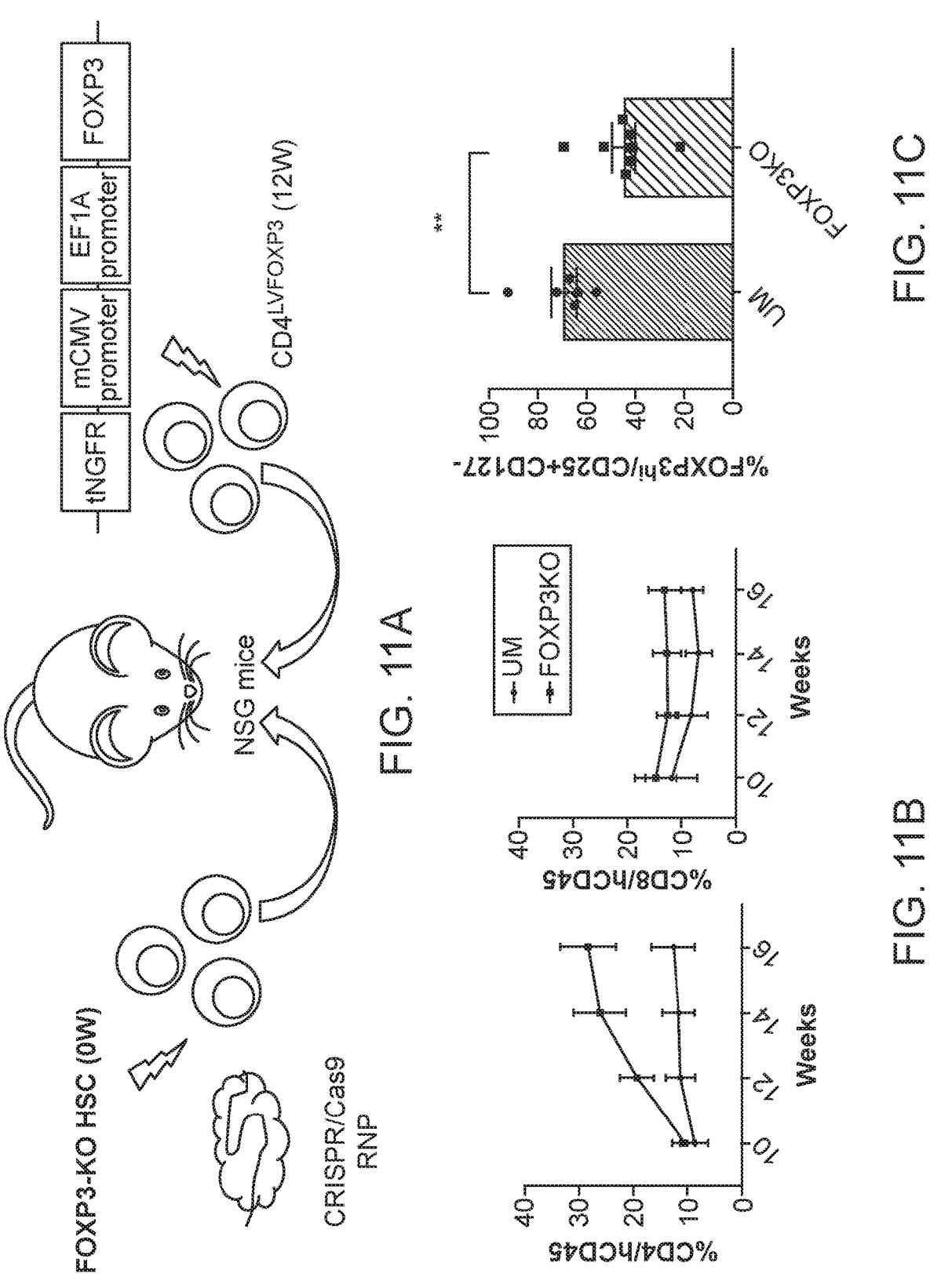
FIG. 11 Diagram of the FOXP3-deficient hu-mouse model (a) in which FOXP3 is KO using CRISPR/Cas9 RNP in human CD34+ HSPCs (HSC) and the resulting cells engraft and reconstitute an immunodeficient mouse (NSG or SGM3-NSG), leading to increased CD4+ T cell lymphoproliferation (b) and reduced FOXP3+/CD25+/CD127neg Treg cells (c).

In addition, the mice injected with CD4$^{LVFOXP3}$ were resistant to further injections (re-challenge) of a second subset of Teff cells, suggesting that CD4$^{LVFOXP3}$ exert an effect on other cells, leading to a decrease in activation and possibly reduced reactivity of other cells (FIG. 11). Therefore, these data suggest an "infectious tolerance" effect on the reactive T cells.

Overall these data show the efficacy of the CD4$^{LVFOXP3}$ in vitro and in vivo, in autologous as well as in the allogeneic setting.

Figures 12D, 12E, 12F:
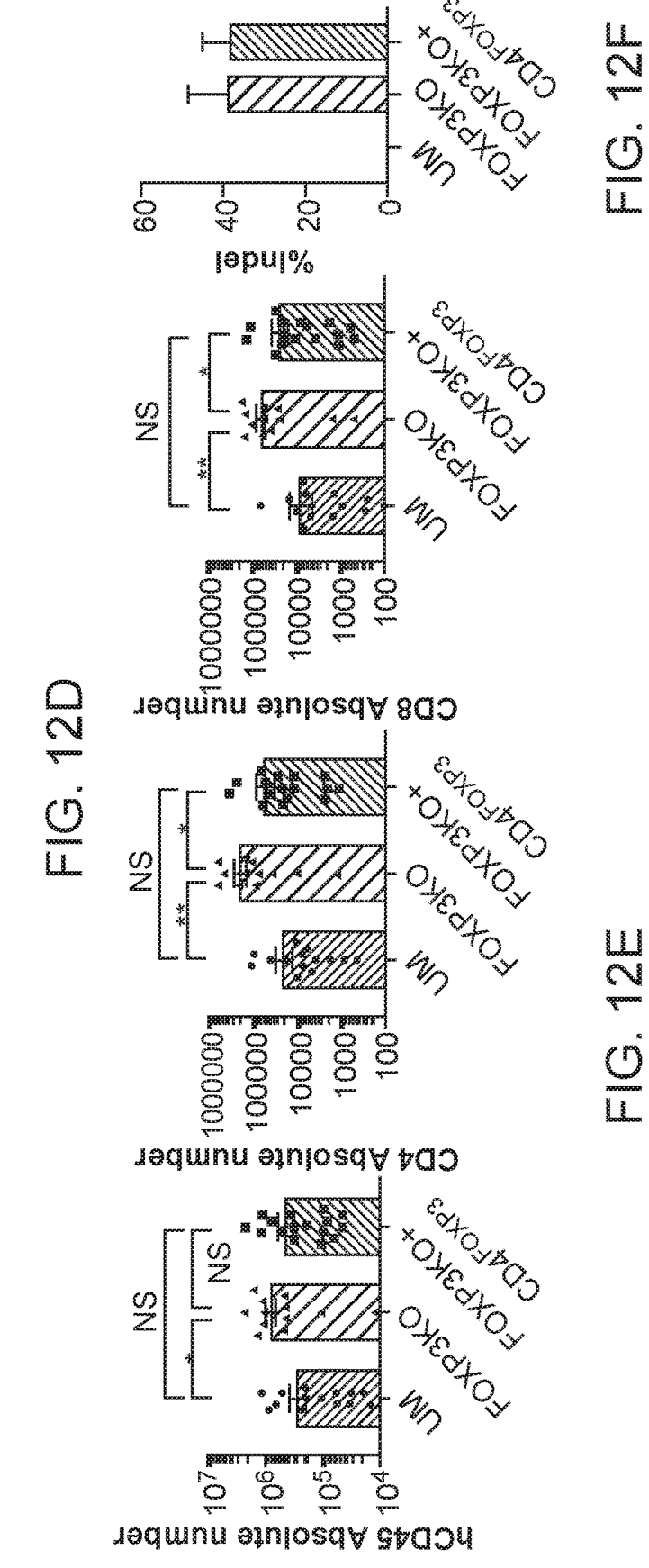
FIG. 12 shows the results obtained using the FOXP3-deficient hu-mouse model, after injecting these mice with CD4$^{LVFOXP3}$. Survival of the mice who received at week 12 the CD4$^{LVFOXP3}$ was better as compared to those reconstituted with FOXP3-deficient HSC (a). Despite the transduced T cells slowly decreased in the peripheral blood of the mice (b), the animal that received CD4$^{LVFOXP3}$, normalized their engraftment (c), CD4 and CD8 percentages and absolute numbers (d and e).
Figures 13A, 13B, 13C, 13D, 13E:
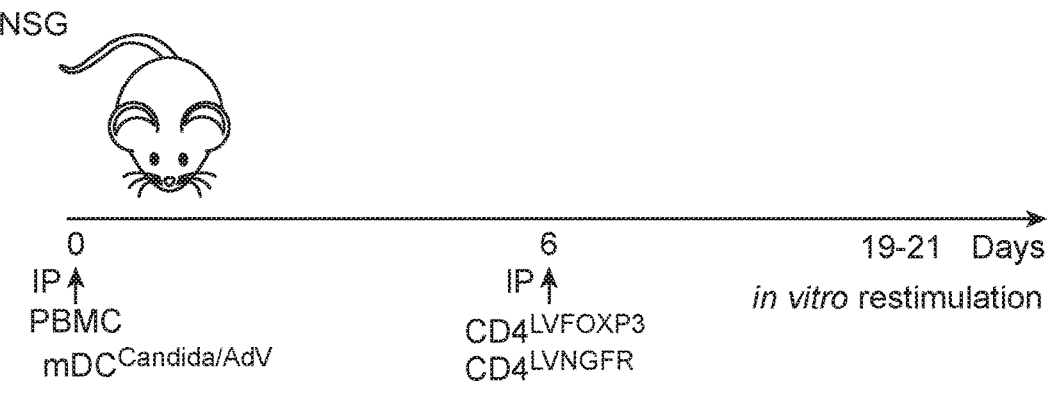
FIG. 13. Shows the experimental protocol (a) and the results of the experiments assessing the impact of CD4$^{LVFOXP3}$ injection on the expansion of an immune response to pathogens such as *Candida albicans* (b and c) or adenovirus (d and e), using PBMC+ mature dendritic cells (mDC) pulsed with the antigen. Mice injected with CD4$^{LVFOXP3}$ preserved an immune response that was comparable to that of control mice uninjected or injected with NGFR transduced cells. Results are expressed as IFNγ+ cells determined by Elispot.

We established: i) a method to assess the efficacy of CD4$^{LVFOXP3}$ T cells in preventing and controlling lymphoproliferation of FOXP3 deficient CD4+ T cells whereby these cells are obtained from healthy donors CD34+ HSPCs in which FOXP3 has been knocked-down by CRISP-Cas9 RNP specifically targeting FOXP3 or from IPEX patients' CD34+ HSPCs. The FOXP3 deficient HSPCs are then transplanted intrahepatically in 3-5 days old pups of immune deficient mice (NSG or SGM3_NSG) and differentiate into an immune system with reduced/absent FOXP3 expression (FIG. 12). ii) a method to assess the impact of the CD4$^{LVFOXP3}$ T cells on completion and expansion of an immune response to pathogens, including but not limited to fungi (*Candida albicans*), virus (adenovirus), using huPBL-mice model (FIG. 13); and iii) a method to assess the impact of CD4$^{LVFOXP3}$ T cells on immunesurvelliance and tumor clearance in a skin sarcoma hu-mouse model (FIG. 14).

Figures 15A, 15B:
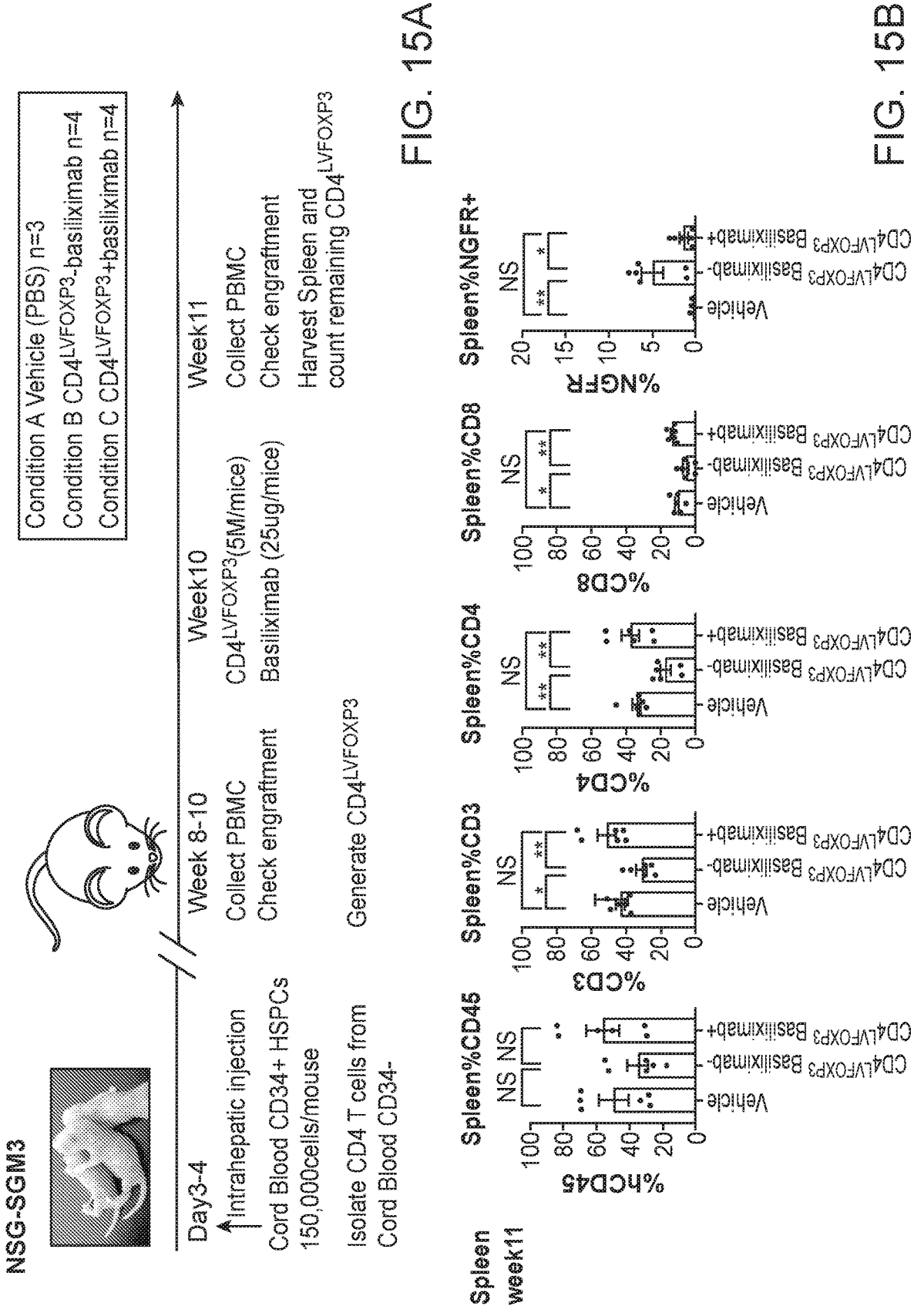
FIG. 15 shows the experimental design (a) and results of in vivo reduction of the CD4$^{LVFOXP3}$ upon in vivo exposure to Basiliximab, indicating that this drug could be used in vivo to eliminate the CD4$^{LVFOXP3}$ in case of undesired toxicity.
Figure 16:
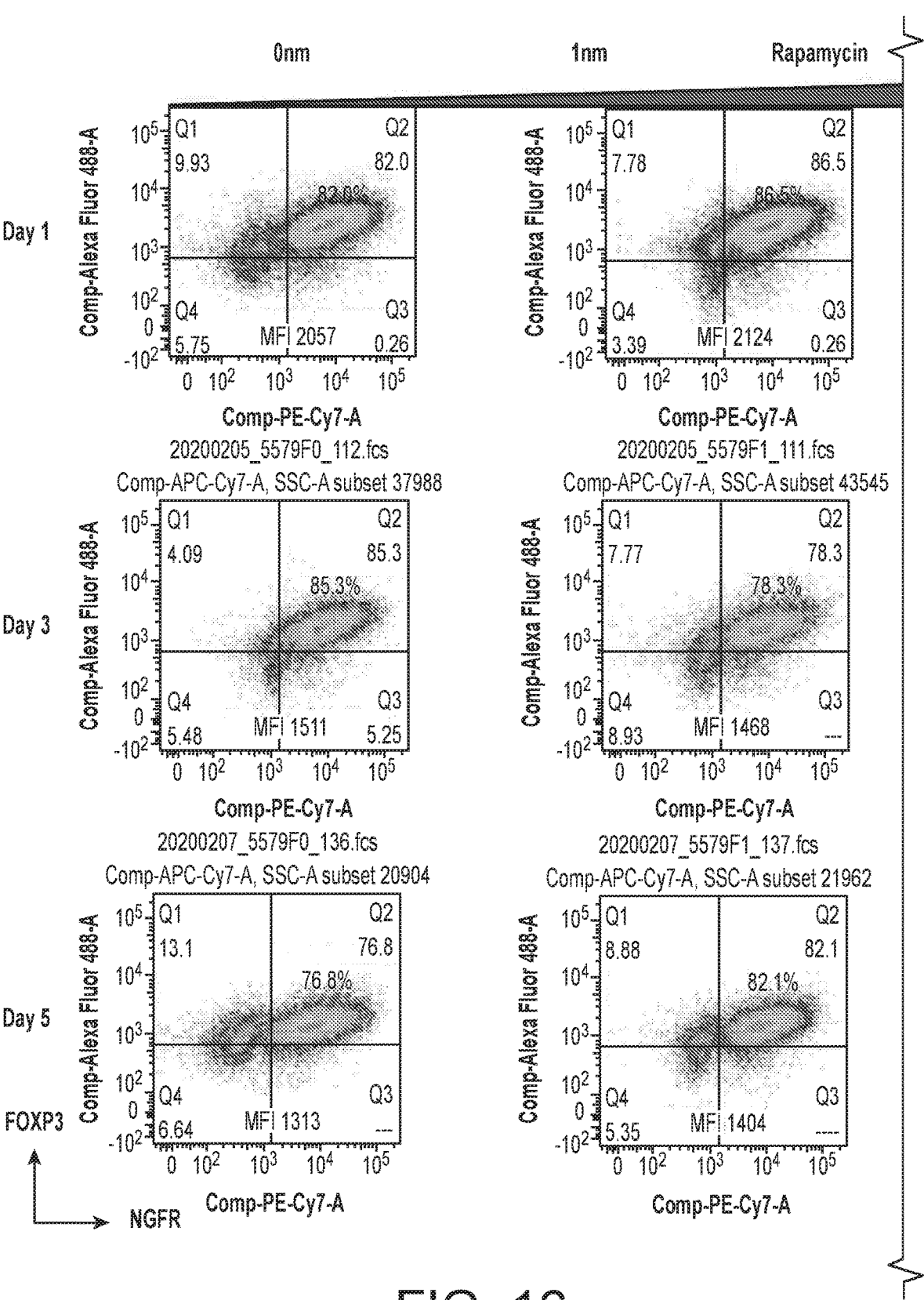
FIG. 16 shows in vitro phenotypic stability and survival of the CD4$^{LVFOXP3}$ in the presence of rapamycin, indicating that CD4$^{LVFOXP3}$ could be administered together with rapamycin without this drug negatively affecting the CD4$^{LVFOXP3}$.
Figure 16:
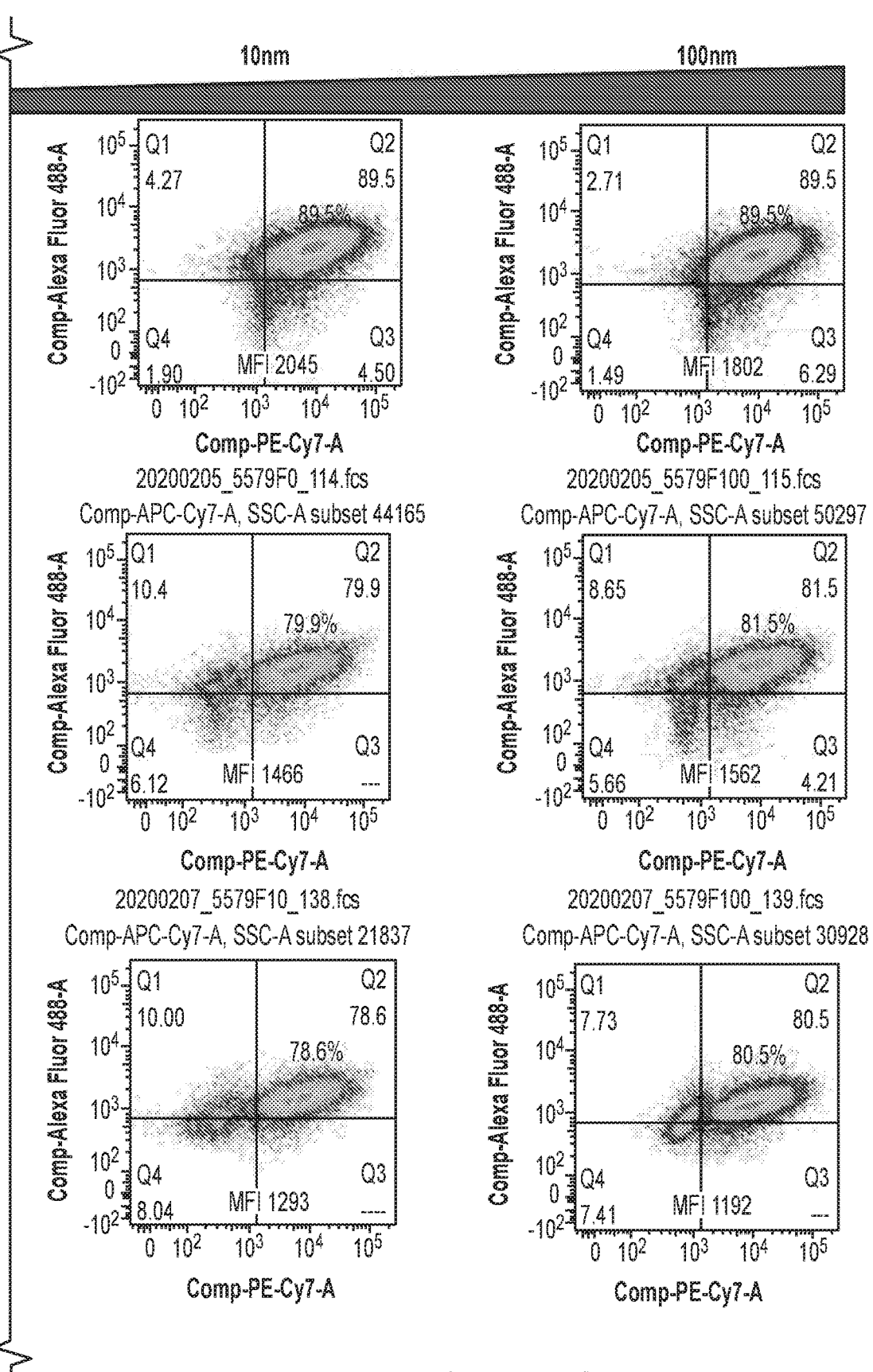

CD4$^{LVFOXP3}$ T cells express high and stable levels of CD25 on the membrane that is directly regulated by FOXP3. Therefore, we have successfully demonstrated (FIG. 15) that these cells can be eliminated in vivo by administration of anti-CD25 mAb Basiliximab, commercially available and in use in pediatric and adult patients undergoing transplantation.

CD4$^{LVFOXP3}$ T cells have a stable phenotype even in the presence of rapamycin (FIG. 18).

The immune system of IPEX patients manifests multiple immune defects which have been described in other autoimmune diseases not caused by FOXP3 mutations. Specifically, increased T lymphocyte numbers, increased autoreactive B cells with autoantibody production, increased IL-17 producing T cells, increased T follicular helper cells, increased T helper cells' cytokines (increased IFNγ, IL-17, IL-23) are all common hallmarks of autoimmunity. Therefore, even if CD4$^{LVFOXP3}$ have not been used in vivo, there are data supporting the beneficial effect of the clinical use of Treg cells of different origin to safely regulate uncontrolled immune responses and clinical manifestations commonly observed in IPEX syndrome (Bluestone Science, 2018; Esensten J H JACI, 2018).

Adoptive transfer of polyclonal CD4$^+$CD25$^+$FOXP3$^+$ Treg cells has proven to be safe and showed some level of efficacy in clinical trials. Numerous Treg trials have been recently completed or are currently being conducted in a variety of diseases including Inflammatory Bowel Disease, autoimmune hepatitis, skin autoimmune diseases and allergy (Esensten J H, 2018).

Several groups have applied polyclonal CD4$^+$CD25$^+$ Tregs containing a high proportion of FOXP3$^+$ T cells, either freshly isolated or ex-vivo expanded, with the aim of preventing GvHD after allogenic-HSCT for onco-haematological diseases. The results showed that the overall procedure is feasible and safe. One trial reported decreased incidence of grade II-IV GvHD as compared to historical controls in patients receiving umbilical-cord-blood-derived Tregs, without increased incidence of infections (Brunstein et al., 2011). Data were confirmed in a more recent trial from the same group, in which the clinical outcome of patients receiving Treg-based cell therapy was compared with that of control patients who received the same conditioning regimen and immunosuppressive treatment but no Tregs. The incidence of grade II-IV acute-GvHD at 100 days was 9% vs 45% in controls, whereas chronic-GvHD at 1 year was zero in treated patients (Brunstein et al., 2016). The Treg treatments were well tolerated without any suspected adverse events, even at the highest cell dose of 100×10$^6$ cells/kg, and no increase in the number or severity of infections in the Treg treated cohort was observed.

In a third trial, patients undergoing allogenic-HSCT who were injected with freshly isolated peripheral Tregs showed low grade GvHD and no development of chronic-GvHD (Di Ianni et al., 2011). More recently, the same group showed reduced incidence of disease relapse in Treg-treated patients (Martelli et al., 2014).

These initial results encouraged a wider application of Tregs as therapy after solid organ transplantation. Several trials are currently ongoing, although final results are not currently available (Vaikunthanathan et al., 2017b). Among those, in The-ONE-Study, a Phase 1/2 dose-escalation study, several subtypes of Tregs, including ex-vivo expanded FOXP3$^+$-Tregs, have been infused in patients undergoing kidney transplant with the goal of avoiding life-long immunosuppression through the induction of active tolerance (NCT02129881) (Leslie, 2011; Vaikunthanathan et al., 2017b). Similarly, a Treg-immunotherapy trial in the setting of liver transplantation, ThRIL (NCT02166177), has been initiated, although safety data are not yet available (Safinia et al., 2016).

FOXP3$^+$-Treg-based therapy was safely tested also in the context of autoimmune diseases. In a trial limited to a few patients, ex-vivo expanded autologous CD4$^+$ CD25$^{hi}$CD127$^-$ Tregs were administered to children with recent-onset T1D (Marek-Trzonkowska et al., 2012), and more recently to new-onset adult T1D patients (Bluestone et al., 2015). In both cases the procedure appeared to be feasible and safe, as no toxicities or serious adverse events attributable to the infusion were reported in up to one year follow up, although published data do not provide conclusions on efficacy. In the first trial, patients were treated with 10-20×10$^6$ cells/kg, which resulted in a statistically significant lower insulin requirement and higher C peptide laboratory measure when compared to matched control subjects, while 2 of 12 treated patients became insulin independent. Importantly, in the latter trial, safety was demonstrated for transfer of high number of Tregs (up to 2.6×10$^9$ cells/kg) (Bluestone et al., 2015). Several patients post Treg infusion had stable, improved C peptide levels and insulin use for up to 2 years after a single Treg injection, although the study was not powered to determine efficacy.

Overall, the data available support the safety of the Treg cell therapy approach. However, the cells manufactured in the previous studies were not stable in inflammatory conditions and their in vivo survival was limited and difficult to assess. The potential advantage of the proposed CD4$^{LVFOXP3}$ is that they are phenotypically stable. CD4$^{LVFOXP3}$ can also be traced via cell surface expression of NGFR encoded in the LV that contains the FOXP3 gene. The efficacy of CD4$^{LVFOXP3}$ is a medical breakthrough in treatment of patients with IPEX and will inform us about the response of clinical manifestations of the disease (T1D and other endocrinopathies, inflammatory bowel disease (IBD), eczema or psoriasis-like dermatitis, cytopenia) over time. This information is key for the design of future indications.

Example 7

Specifications of New LVFOXP3 Construct

To obtain CD4$^{LVFOXP3}$ by FOXP3 gene transfer into autologous CD4$^+$ T cells we have developed a third-generation bidirectional lentiviral vector containing the full-length cDNA of FOXP3, expressed under an EF1α promoter and NGFR, a marker gene, expressed under the minimal CMV promoter from the opposite strand, providing a cell surface marker for selection of transduced cells, and a robust method of gene transduction in CD4$^+$ T cells followed by purification and expansion of the CD4$^{LVFOXP3}$.

The LVFOXP3 vector construct underwent improvements relative to the vector described in the publication Passerini L. et al Sci Transl Med. (2013) 5(215):215ra174) that reduced the size, enhanced efficiency of production, and made this construct suitable and safer for clinical use. These modifications consisted of CAP binding site/AC promoter and HA tag removal; AmpR replacement with KanaR; and replacement of wildtype WPRE with a mutated WPRE, and are shown in FIGS. 2A and 2B.

The pre-clinical data available to date demonstrates that LVFOXP3 provides efficient functional gene transduction in CD4$^+$ obtained from both healthy individuals and IPEX patients with different FOXP3 mutations. In addition, we showed functional equivalence using CD4$^{LVFOXP3}$ allogenic or autologous to the responder effector T cells. To improve safety, basiliximab, an anti-CD25 mAb, can be used to eliminate CD4$^{LVFOXP3}$ cells in the event of unacceptable toxicity.

Example 8

Clinical Trial

We propose that administration of autologous CD4$^+$ T cells converted into CD4$^{LVFOXP3}$ by LV-mediated FOXP3 gene transfer to patients with IPEX reduces autoreactivity and immune dysregulation, therefore offering an improved therapeutic approach that circumvents the requirement for generalized immunosuppression and avoids the risks of allogenic hematopoietic stem cell transplant (HSCT), or at least would ameliorate the patient's clinical status without additional organ damage, favoring a better outcome for HSCT, when available. We have successfully converted healthy donor CD4$^+$ T cells into Treg cells using the LV-mediated FOXP3 gene transfer as described above.

A key advantage to autologous cell therapy is that wild-type FOXP3 is delivered to the patient's own CD4$^+$ T cells, containing also the pathogenic T cells. These autologous engineered cells are infused to restore immune regulation. In addition, the autologous CD4$^{LVFOXP3}$ are functionally stable, since they constitutively express FOXP3, and they might alone be sufficient to immune regulate, allowing reduction or avoidance of pharmacologic immunosuppression.

A standard 3+3 dose escalation design is used in the clinical trial. Three to 6 patients per dose-cohort are treated at each dose of CD4$^{LVFOXP3}$ (1×10$^6$ cells/kg, 3×10$^6$ cells/kg, and 10×10$^6$ cells/kg). The starting dose level of 1×10$^6$ cells/kg was chosen based on previous experience with freshly isolated or expanded Treg cell therapy. Indeed, expanded autologous Treg cells administered in T1D patients have been shown to be safe even at doses of 10$^9$/kg. However, since our cell product is FIH, is genetically modified and we plan to treat acutely ill pediatric patients with very diverse age and weight, we chose this conservative low dose. In addition, a 28 day safety assessment period after the first patient in each dose cohort and prior to escalation to the next dose cohort will occur to evaluate dose limiting toxicities (DLTs). All other infusions in each dose cohort are staggered by at least fourteen (14) days to allow for adequate safety assessment.

Although this study is a first-in-human trial, because of the lethal nature of this disease, the median age of surviving individuals with IPEX, and the lack of alternative curative options, the safety of CD4$^{LVFOXP3}$ is evaluated in patients of all ages. We propose that the first patient in the first dose cohort is 12 years of age or older, and if tolerated (no dose limiting toxicity observed), all other patients is enrolled irrespective of age. Patients enrolled in the study will not change their current pharmacological therapy, unless receiving steroids, in which case the dose of steroids must be less than 0.5 mg/kg/day in order for the patient to be eligible for participation in this trial.

The study is designed to evaluate the feasibility of manufacturing CD4$^{LVFOXP3}$ to meet the targeted dose level and established release criteria, and determine the maximum tolerated dose (MTD) of autologous CD4$^{LVFOXP3}$ in subjects with IPEX who are affected by Treg cell deficiency due to FOXP3 mutation. In addition, the impact of CD4$^{LVFOXP3}$ T cell on the clinical manifestations in IPEX patients are assessed. The administration of autologous CD4$^+$ T cells converted into CD4$^{LVFOXP3}$ by LV-mediated FOXP3 gene transfer administered to patients with IPEX is expected to reduce autoreactivity, inflammation and immune dysregulation; thereby, offering a therapeutic approach that circumvents the requirement for generalized immunosuppression and avoids the risks of allogenic HSCT, or when a suitable donor is available, may stabilize the patient's clinical condition to minimize the risk of transplant. In addition, CD4$^{LVFOXP3}$ could also be given after hematopoietic stem cell transplantation to boost immune regulation and control rejection (disease relapse) that is often observed in IPEX patients.

What is claimed is:

1. A pharmaceutical composition comprising a unit dose of CD4$^{LVFOXP3}$ T cells produced by the method comprising:
   i) obtaining a biological sample comprising CD4+T lymphocytes from a subject;

ii) activating the CD4$^+$ T cells for up to 24 hours in medium comprising IL-2, IL-7, and anti-CD3 and anti-CD28 coated nanomatrix in the absence of antigen-presenting cells;
   iii) transducing the CD4+T lymphocytes in the absence of polybrene with a recombinant lentiviral vector comprising full-length FOXP3 cDNA wherein the recombinant lentiviral vector is a bidirectional lentiviral vector of not more than 10,500 bp comprising full-length FOXP3 cDNA expressed under an EF1a promoter and NGFR expressed under minimal CMV promoter from the opposite strand vector, comprising:
      a) a polynucleotide encoding forkhead box protein 3 (FOXP3);
      b) an elongation factor 1 a (EF1 a) promoter, wherein the EF1 a promoter is operably linked to the polynucleotide encoding FOXP3;
      c) a polynucleotide encoding NGFR;
      d) a modified Woodchuck hepatitis virus posttranscriptional regulatory element (WPRE) modified to remove a WHx start codon;
      e) human immunodeficiency virus (HIV)-derived elements comprising a 5' long terminal repeat (5' LTR), a Y packaging signal, a truncated Gag sequence, a rev response element (RRE) sequence, a central polypurine tract (cPPT), a central termination sequence (CTS), a truncated negative regulatory factor (NEF) sequence, and a SIN 3' long terminal repeat (3' LTR);
      f) a polyadenylation sequence;
      g) an SV40 origin of replication;
      h) a bacterial high copy origin of replication (Ori); and
      i) kanamycin resistance gene;
   iv) culturing the CD4$^+$ T lymphocytes in medium comprising IL-2, IL-15 and anti-CD3 and anti-CD28 coated nanomatrix in the absence of antigen-presenting cells for a period of from 5 to 15 days, wherein the CD4$^+$ T lymphocytes are converted into the Treg-like cells (CD4$^{LVFOXP3}$ T cells); and
   v) purifying CD4$^{LVFOXP3}$ T cells following step iv) by positive immunomagnetic selection to obtain a cell population of greater than 85% purity;
   and a pharmaceutically acceptable excipient.

2. The composition of claim 1, wherein the biological sample comprises peripheral blood lymphocytes.

3. The composition of claim 1, wherein following step (i), CD4$^+$ T lymphocytes are isolated from the biological sample by immunomagnetic separation.

4. The composition of claim 1, wherein the CD4$^{LVFOXP3}$ T cells are purified following step iii) by immunomagnetic selection for NGFR.

* * * * *